US007744604B2

(12) United States Patent
Maitland et al.

(10) Patent No.: US 7,744,604 B2
(45) Date of Patent: Jun. 29, 2010

(54) SHAPE MEMORY POLYMER MEDICAL DEVICE

(75) Inventors: Duncan Maitland, Pleasant Hill, CA (US); William J. Benett, Livermore, CA (US); Jane P. Bearinger, Livermore, CA (US); Thomas S. Wilson, San Leandro, CA (US); Ward Small, IV, Livermore, CA (US); Daniel L. Schumann, Concord, CA (US); Wayne A. Jensen, Livermore, CA (US); Jason M. Ortega, Pacifica, CA (US); John E. Marion, III, Livermore, CA (US); Jeffrey M. Loge, Stockton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1196 days.

(21) Appl. No.: 11/172,668

(22) Filed: Jun. 30, 2005

(65) Prior Publication Data
US 2006/0009785 A1    Jan. 12, 2006

Related U.S. Application Data

(63) Continuation-in-part of application No. 10/713,622, filed on Nov. 13, 2003, now Pat. No. 7,291,154.

(60) Provisional application No. 60/641,961, filed on Jan. 6, 2005.

(51) Int. Cl.
*A61F 11/00* (2006.01)
(52) U.S. Cl. ..................................................... 606/108
(58) Field of Classification Search .................. 606/108, 606/159, 151, 153, 157, 113, 114, 127, 200
See application file for complete search history.

(56) References Cited

U.S. PATENT DOCUMENTS

| 3,868,956 | A | 3/1975 | Alfidi, et al. |
| 3,996,938 | A | 12/1976 | Clark, III |
| 4,140,126 | A | 2/1979 | Choudhury |
| 4,706,671 | A | 11/1987 | Weinrib |
| 4,873,978 | A | 10/1989 | Ginsburg |
| 5,011,488 | A | 4/1991 | Ginsburg |
| 5,049,591 | A | 9/1991 | Hayashi et al. |
| 5,102,415 | A | 4/1992 | Guenther et al. |
| 5,330,483 | A | 7/1994 | Heaven et al. |
| 5,370,609 | A | 12/1994 | Drasler et al. |
| 5,411,509 | A | 5/1995 | Hilal |
| 5,490,859 | A | 2/1996 | Mische et al. |

(Continued)

FOREIGN PATENT DOCUMENTS

EP          0337918 B1    11/1994

(Continued)

*Primary Examiner*—Kevin T Truong
(74) *Attorney, Agent, or Firm*—Eddie E. Scott; John H. Lee

(57) ABSTRACT

A system for removing matter from a conduit. The system includes the steps of passing a transport vehicle and a shape memory polymer material through the conduit, transmitting energy to the shape memory polymer material for moving the shape memory polymer material from a first shape to a second and different shape, and withdrawing the transport vehicle and the shape memory polymer material through the conduit carrying the matter.

2 Claims, 28 Drawing Sheets

U.S. PATENT DOCUMENTS

| | | |
|---|---|---|
| 5,603,722 A | 2/1997 | Phan et al. |
| 5,645,564 A | 7/1997 | Northrup et al. |
| 5,674,242 A | 10/1997 | Phan et al. |
| 5,762,630 A | 6/1998 | Bley et al. |
| 5,792,157 A | 8/1998 | Mische et al. |
| 5,836,868 A | 11/1998 | Ressemann et al. |
| 5,843,118 A | 12/1998 | Sepetka et al. |
| 5,846,247 A | 12/1998 | Unsworth et al. |
| 5,895,398 A | 4/1999 | Wensel et al. |
| 5,897,567 A | 4/1999 | Ressemann et al. |
| 5,902,518 A | 5/1999 | Khazai et al. |
| 5,910,357 A | 6/1999 | Hachisuka et al. |
| 5,957,966 A | 9/1999 | Schroeppel et al. |
| 5,964,744 A | 10/1999 | Balbierz et al. |
| 6,022,309 A | 2/2000 | Celliers et al. |
| 6,086,599 A | 7/2000 | Lee et al. |
| 6,090,072 A | 7/2000 | Kratoska et al. |
| 6,102,917 A * | 8/2000 | Maitland et al. ............ 606/108 |
| 6,102,933 A | 8/2000 | Lee et al. |
| 6,120,515 A | 9/2000 | Rogers et al. |
| 6,740,094 B2 * | 5/2004 | Maitland et al. ............ 606/108 |
| 2003/0236533 A1 | 12/2003 | Wilson et al. |

FOREIGN PATENT DOCUMENTS

| | | |
|---|---|---|
| EP | 0472368 B1 | 6/1995 |
| WO | WO 00/03643 | 1/2000 |

* cited by examiner (a)
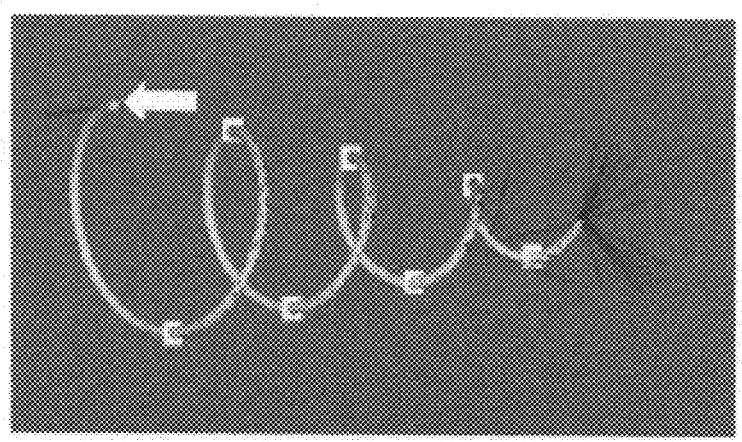
(b)
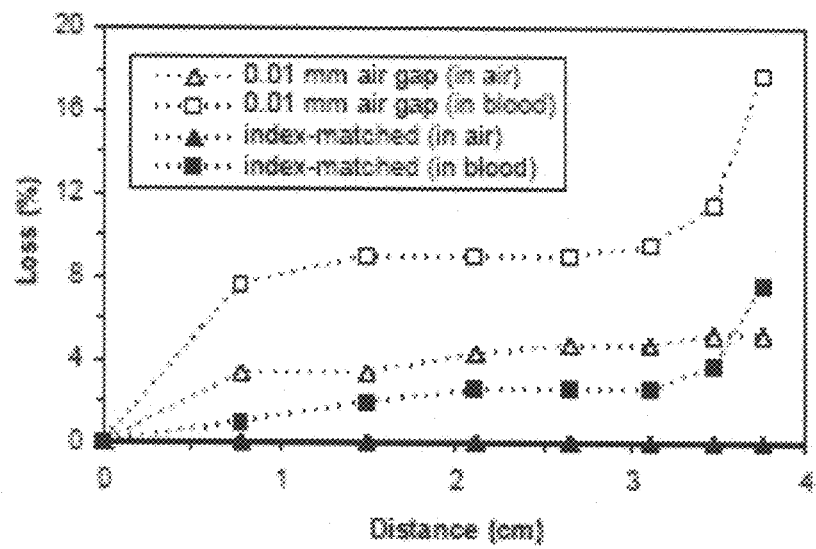
FIG. 27

SHAPE MEMORY POLYMER MEDICAL DEVICE

CROSS-REFERENCE TO RELATED APPLICATIONS

This application is a Continuation-in-Part of U.S. patent application Ser. No. 10/713,622 filed Nov. 13, 2003 now U.S. Pat. No. 7,291,154, titled, "Shape Memory Polymer Actuator and Catheter" published as United States Patent Application No. 2004/0133231 Jul. 8, 2004. U.S. patent application Ser. No. 10/713,622 is incorporated herein in its entirety by this reference.

This application claims the benefit of U.S. Provisional Patent Application No. 60/641,961 filed Jan. 6, 2005 and titled "Shape Memory Polymer Device for Occlusion Removal." U.S. Provisional Patent Application No. 60/641,961 filed Jan. 6, 2005 and titled "Shape Memory Polymer Device for Occlusion Removal" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to medical devices and more particularly to a shape memory polymer medical device.

2. State of Technology

U.S. Pat. No. 5,836,868 for an expandable intravascular occlusion material removal devices and methods of use, by Ressemann, et al., patented Nov. 17, 1998, provides the following description: "The present invention generally relates to constructions for intravascular treatment devices useful for removing vascular occlusion material from a vascular occlusion or from a vascular lumen. The invention more specifically relates to expandable intravascular occlusion material removal devices, as well as to methods of using those devices to treat vascular diseases.

Vascular diseases, such as atherosclerosis and the like, have become quite prevalent in the modern day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop non-invasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further non-invasive, intravascular treatments exist that are not only pharmaceutical, but also revascularize blood vessels or lumens by mechanical means. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site."

U.S. Pat. No. 5,102,415, for an apparatus for removing blood clots from arteries and veins, by Guenther, et al., patented Apr. 7, 1992, provides the following description: "A triple catheter for removing of blood clots from arteries and veins is equipped with an outer catheter that can be inserted into a blood vessel and an inner catheter with an inflatable balloon at its distal end that can be inserted into the outer catheter. The inner catheter is surrounded by an intermediate catheter also inserted into the outer catheter. The intermediate catheter has a radially expandable distal end receptacle made of an elastic mesh structure of spring wires or plastic monofilaments covered by or embedded in an elastic plastic coating. A very small puncture channel is required for the insertion of such a triple catheter through the wall of a blood vessel."

U.S. Pat. No. 5,645,564 for microfabricated therapeutic actuator mechanisms, by Northrup, et al., patented Jul. 8, 1997, provides the following description: "Electromechanical microstructures (microgrippers), either integrated circuit (IC) silicon-based or precision machined, to extend and improve the application of catheter-based interventional therapies for the repair of aneurysms in the brain or other interventional clinical therapies. These micromechanisms can be specifically applied to release platinum coils or other materials into bulging portions of the blood vessels also known as aneurysms. The "micro" size of the release mechanism is necessary since the brain vessels are the smallest in the body. Through a catheter more than one meter long, the micromechanism located at one end of the catheter can be manipulated from the other end thereof. The microgripper (micromechanism) of the invention will also find applications in non-medical areas where a remotely actuated microgripper or similar actuator would be useful or where micro-assembling is needed."

U.S. Pat. No. 6,102,917 for a shape memory polymer (SMP) gripper with a release sensing system, by Maitland, et al., patented Aug. 15, 2000, provides the following description: "A system for releasing a target material, such as an embolic coil from an SMP located at the end of a catheter utilizing an optical arrangement for releasing the material. The system includes a laser, laser driver, display panel, photodetector, fiber optics coupler, fiber optics and connectors, a catheter, and an SMP-based gripper, and includes a release sensing and feedback arrangement. The SMP-based gripper is heated via laser light through an optic fiber causing the gripper to release a target material (e.g., embolic coil for therapeutic treatment of aneurysms). Various embodiments are provided for coupling the laser light into the SMP, which includes specific positioning of the coils, removal of the fiber cladding adjacent the coil, a metal coating on the SMP, doping the SMP with a gradient absorbing dye, tapering the fiber optic end, coating the SMP with low refractive index material, and locating an insert between the fiber optic and the coil."

U.S. Pat. No. 5,843,118 for fibered micro vaso-occlusive devices, by Sepetka, et al., patented Dec. 1, 1998, provides the following description: "This is a vaso-occlusive device made up of at least one short retainer and a longer fiber bundle. The retainer may be radio-opaque. The fibers may be straight, looped, or tufted. The primary use of the device is in the very small vessels at the distal portion of the vasculature."

U.S. Pat. No. 5,895,398 for a method of using a clot capture coil, by Wensel, et al., patented Apr. 20, 1999, provides the following description: "A clot and foreign body removal device is described which comprises a catheter with at least one lumen. Located within the catheter is a clot capture coil that is connected to an insertion mandrel. In one embodiment, the clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. In another embodiment the coil is a biphasic coil which changes shape upon heating or passing an electric current. Once the coil configuration has been established, the coil can be used to ensnare and corkscrew a clot in a vessel. A clot is extracted from the vessel by moving the clot capture coil and catheter proximally until the clot can be removed or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed."

Patents and patent applications that provide additional background information include: U.S. Pat. No. 3,868,956 to Alfidi, Ralph J. and Cross, William B., "Vessel Implantable Appliance and Method of Implanting It," Mar. 4, 1975; U.S. Pat. No. 3,996,938 to Clark, W.T, "Expanding Mesh Catheter," Dec. 14, 1976; U.S. Pat. No. 4,140,126 to Choudhury, M.H., "Method for Performing Aneurysm Repair," Feb. 20, 1979; U.S. Pat. No. 4,706,671 to Weinrib, H.P., "Catheter with Coiled Tip," Nov. 17, 1987; U.S. Pat. No. 4,873,978 to Ginsburg, R., "Device and Method for Emboli Retrieval," Oct. 17, 1989; U.S. Pat. No. 5,011,488 to Ginsburg, R., "Thrombus Extraction System," Apr. 30, 1991; U.S. Pat. No. 5,049,591 to Hayashi, S. and Fujimori, H. "Shape Memory Polymer Foam," Sep. 17, 1991; U.S. Pat. No. 5,102,415 to Guenther, R.W. and Vorwerk, D., "Apparatus for Removing Blood Clots from Aarteries and Veins," Apr. 7, 1992; U.S. Pat. No. 5,330,483 to Heaven, M.D., and Schuler, M., "Specimen Reduction Device," Jul. 9, 1994; U.S. Pat. No. 5,370,609 to Drasler, W.J., Dutcher, R.G., Jenson, M.L., Thielen, J.M., Protonotarios, E.I., "Thrombectomy Device," Dec. 6, 1994; U.S. Pat. No. 5,411,509 to Hilal, S., "Embolectomy Catheter," May 2, 1995; U.S. Pat. No. 5,490,859 to Mische, H.A., Ressemann, T.V., Vrba, A.C., and Hackett, S.S., "Expandable Intravascular Occlusion Materials Removal Devices and Methods of Use," Feb. 13, 1996; U.S. Pat. No. 5,603,722 to Phan, L., Froix, M. and Stertzer, S., "Intravascular Stent," Feb. 18, 1997; U.S. Pat. No. 5,674,242 to Phan, L., et al., "Endoprosthetic Device With Therapeutic Compound," Oct. 7, 1997; U.S. Pat. No. 5,762,630 to Bley, R., and Kubacki, G., "Thermally Softening Stylet," Jun. 9, 1998; U.S. Pat. No. 5,792,157 to Mische, H.A., Ressemann, T.V., Hoium, S.A., "Expandable Intravascular Occlusion Material Removal Devices and Methods of Use," Aug. 11, 1998; U.S. Pat. No. 5,846,247 to Unsworth, J.D., and Waram, T.C., "Shape Memory Tubular Deployment System," Dec. 8, 1998; U.S. Pat. No. 5,897,567 to Ressemann, T.V., Vrba, A.C., Hackett, S.S., Kugler, C.J., Mische, H.A., "Expandable Intravascular Occlusion Material Removal Devices and Methods of Use," Apr. 27, 1999; U.S. Pat. No. 5,902,518 to Khazai, B. and Nichols, G.M., "Self-regulating Polymer Composite Heater," May 11, 1999; U.S. Pat. No. 5,910,357 to Hachisuka, H., Kondo, Y., Ikeda, K., Takano, H., Mochisuki, H., "Separation Membrane and Method of Producing the Same, and Shape Memory Composition," Jun. 8, 1999; U.S. Pat. No. 5,957,966 to Schroeppel, E.A., Spehr, P.R., and Machek, J.E., "Implantable Cardiac Lead with Multiple Shape Memory Polymer Structures," Sep. 28, 1999; U.S. Pat. No. 5,964,744 to Balbierz, D.J. Walker, J.M., Thomas, J.R., Bley, R.S., Van Bladel, K., "Polymeric Medical Devices Having Shape Memory," Oct. 12, 1999; U.S. Pat. No. 6,022,309 to Celliers, P., Da Silva, L., Glinsky, M., London, R., Maitland, D., Matthews, D., Fitch, P., "Optoacoustic Thrombolysis," Feb. 8, 2000; U.S. Pat. No. 6,086,599 to Lee, A.P., Fitch, "Micro Devices Using Shape Memory Polymer Patches for Mated Connections," Jul. 11, 2000; U.S. Pat. No. 6,090,072 to Kratoska, W.F., Tay, S.-W., Thorne, S.P., Keith, P.T., "Expandable Introducer Shealth," Jul. 18, 2000; U.S. Pat. No. 6,102,933 to Lee, A.P., Northrup, A., Ciarlo, D.R., Krulevitch, P.A., and Bennett, W.J., "Release Mechanism Utilizing Shape Memory Polymer material," Aug. 15, 2000; U.S. Pat. No. 6,120,515 to Rogers, L., Buckley, J.T., Hundermark, R.R., Powell, F.T., Milo, C., and Castro, A.J., "Composite Atherectomy Cutter," Sep. 19, 2000; EP0337918B1 to Monfort, M.Y, Molenauer, K.M., and Chin, A. K., "Endarectomy Apparatus," Nov. 9, 1994; EP0472368B1: Fearnot, N.E., "Ablation Catheter," Jun. 28, 1995; W00003643: Maitland, D.J., Lee, A.P., Schumann, D.L., and Da Silva, L., "Shape Memory Polymer Gripper with a Release Sensing System," Jan. 27, 2000; U.S. Pat. No. 6,740,094 issued May 25, 2004 to Duncan J. Maitland, Abraham P. Lee, Daniel L. Schumann, Dennis Matthews, Derek Decker for a Shape Memory Polymer Actuator and Catheter; and U.S. Patent Application No. US2003/0236533 by Thomas S. Wilson, Duncan Maitland, Daniel L. Schumann, Steve L. Little, and Paul E. Ahre published Dec. 25, 2003 for a Shape Memory Polymer Actuator and Catheter.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for removing matter from a conduit. The system includes the steps of passing a transport vehicle and a shape memory polymer material through the conduit, transmitting energy to the shape memory polymer material for moving the shape memory polymer material from a first shape to a second and different shape, and withdrawing the transport vehicle and the shape memory polymer material through the conduit carrying the matter. Access to the conduit may be gained using additional means, such as a catheter. The system utilizes a shape memory polymer device for acting upon a material in a conduit. A transport vehicle is adapted to move through the conduit. A shape memory material is operatively connected to the transport vehicle. The transport vehicle with the shape memory polymer material attached may be delivered into the conduit using a catheter or similar means. The shape memory material is adapted to move from a first shape to move through or around the material, to a second and different shape for acting upon the material. A heat transfer mechanism is operatively connected to the shape memory material and is adapted to transfer heat to the shape memory material to move the shape memory material from the first shape to the second shape. The transport vehicle and the shape memory polymer material are withdrawn through the conduit carrying the matter.

Uses of the present invention include, but are not limited to, the removal of obstructions from vascular or non-vascular passageways in the body. Such occlusions may include a thrombus (clot), plaque, fatty deposits, and other natural materials as well as fragments of man made devices. An example of an application is blood clot removal following ischemic stroke.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 27 illustrates the light loss as a function of distance along the shape memory polymer coil.

DETAILED DESCRIPTION OF THE INVENTION

Figure 1:
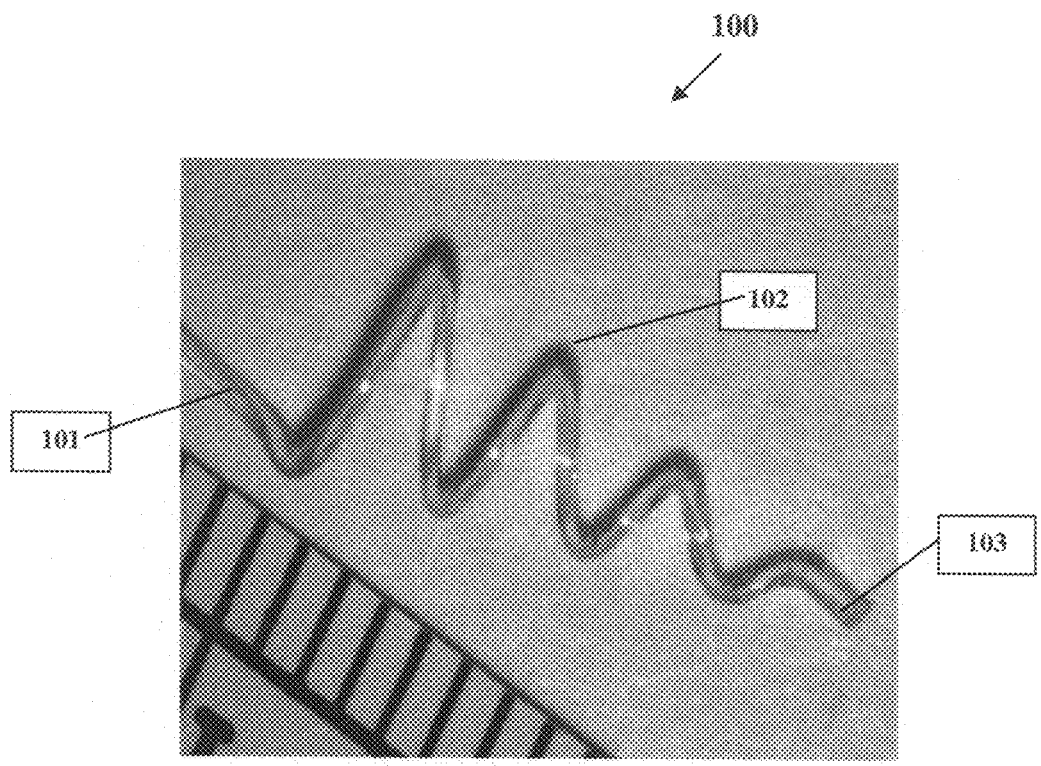
FIG. 1 is an illustration of a shape memory polymer coil of one embodiment of an actuator for acting upon a material in a vessel of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Thromboembolic disorders, such as stroke, pulmonary embolism, thrombosis, and arteriosclerosis are a major cause of morbidity and mortality in the United States. Such disorders are characterized by the partial or complete occlusion of a blood vessel by clots, fatty deposits, or plaque. The tissue downstream of the occluded artery becomes ischemic (oxygen and nutrient deprived). If the occlusion persists, the condition will gradually worsen with time until the cell death (infarction) occurs. The end result, if circulation is not restored, can be loss of limb, angina pectoris, myocardial infarction, stroke, or death.

There are several existing techniques to re-establish flow in occluded vascular passageways and these include balloon angioplasty, balloon embolectomy, and catheter based percutaneous methods such as treatment with thrombolytic drugs, various types of atherectomy, and removal of thromboembolic material with capture coils and like devices.

In balloon angioplasty, a balloon tipped catheter is non-surgically introduced into the vasculature and advanced to the point of occlusion. The balloon section of the catheter is advanced into the stenotic region and next inflated to dilate the blockage. Balloon angioplasty then does not remove the material causing the occlusion, which are subject to future complications such as restenosis or embolic events and is especially unsuitable for smaller vessels.

A common technique for treatment of clots is to place a microcatheter near the clot and infuse a thrombolytic material such as streptokinase, urokinase, or recombinant tissue plasminogen activator (rTPA) to dissolve the clot. However, thrombolysis typically takes hours to days to remove the clot and is typically ineffective unless administered within approximately 3 hours of the thromboembolic event. Thrombolytics also can cause severe hemorrhaging in patients, especially if used after the initial three hour use window, and cannot be used at all in some patients.

One of the first percutaneous methods for recanalization through vascular occlusions involved balloon embolectomy. A catheter with a balloon tip on the distal end is advanced to the site of occlusion through a guide catheter. The distal end is advanced past the site of the occlusion and the balloon is inflated to fill the vascular passageway. It is then pulled back toward the guide catheter, dislodging embolic material from the vascular lumen while doing so. The occluding material is then withdrawn into the guide catheter by the pushing action of the balloon. While devices for balloon embolectomy have improved over the years, there remain problems such as being able to effectively separate material from the vascular lumen and removing the occlusion without it breaking into fragments which can move downstream and lodge in a smaller vessel, causing another thromboembolic event. There are also size limitations on using balloons for expansion of the distal end, preventing this type of device from being usable in small vessels.

Various percutaneous techniques for atherectomy have been developed based on mechanical, hydrodynamic, and acoustic methods for breaking up the occlusion and removal of the resulting debris. For example, several devices have been developed using a high speed rotary abrasion tool comprising abrasive embedded wires or wire meshes which can be controllably expanded by balloon action or longitudinal compression of the wire mesh resulting in circumferential expansion. These devices mechanically grind the occluding material into small fragments which can be withdrawn back up through the catheter via suction. However, such devices are limited to larger size vessels due to limits in construction, being able to move the devices to a smaller tortuous lumen, and in being able to transmit torque once the device falls below a certain size.

Another atherectomy device is described in U.S. Pat. No. 5,370,609 which uses a high velocity jet of saline to create high local shear stresses at the catheter tip, in turn breaking the clot into small pieces. This device has advantages of not having any moving parts, of high speed, flexible for moderate vessels, and good removal of clot debris. However, current designs are unable to be used in vessels smaller than 3 mm, while most embolic strokes occur in vessels smaller than this.

Acoustic wave based thrombectomy devices have also been developed for recanalization of blocked vessels. Acoustic wave generating devices are used at the distal end of the catheter to break the occlusive material into very small pieces, which can then be either suctioned out or in some cases left for re-absorption by the body. Such devices are still experimental and not yet being used commercially.

Embolic coil and other clot capture devices have been developed for thrombectomy as shown by U.S. Pat. Nos. 4,706,671; 4,873,978 and 5,895,398. These devices operate in a manner similar to the balloon embolectomy, but using means for retrieving the clot.

Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while in an elastomeric state and that shape is fixed in one of several ways including cooling the polymer below a crystalline, liquid crystalline, or glass transition temperature; by inducing additional covalent or ionic crosslinking, etc. While in the secondary shape some or all of the polymer chains are perturbed from their equilibrium random walk conformation, having a certain degree of bulk orientation. The oriented chains have a certain potential energy, due to their decreased entropy, which provides the driving force for the shape recovery. However, they do not spontaneously recover due to either kinetic effects (if below their lower glass transition temperature) or physical restraints (physical or chemical crosslinks). Actuation then occurs for the recovery to the primary shape by removing that restraint, e.g., heating the polymer above its glass transition or melting temperature, removing ionic or covalent crosslinks, etc.

The present invention provides a mechanical device to remove non-vascular or vascular occlusions (e.g., blood clot) from the body. The device dimensions depend on the size and location of the occlusion targeted for removal (e.g., a device used to remove a carotid artery occlusion may be larger than a device used to remove an occlusion located further up in the neurovasculature). The preferred embodiment of the device includes: (1) an expandable coil and (2) an expandable basket. Both of these components are constructed of shape memory polymer (SMP), a polymer that can be formed into a primary or equilibrium shape, re-formed into a stable secondary or stressed shape, and actuated by controlled heating to recover its primary shape.

Referring now to the drawings and in particular to FIG. 1, an illustration of a shape memory polymer coil of one embodiment of an actuator for acting upon a material in a vessel of the present invention is shown. The shape memory polymer coil of this embodiment is designated generally by the reference numeral 100. The shape memory polymer coil 100 includes the following structural components: an attachment end 101, a coil corkscrew body 102, and a distal end 103. The attachment end 101 of the shape memory polymer coil 100 is attached to the distal end of a transport vehicle such as a guide wire (not shown). The shape memory polymer coil 100 comprises a shape memory polymer (SMP), a polymer that can be formed into a primary or equilibrium shape, re-formed into a stable secondary or stressed shape, and actuated by controlled heating to recover its primary shape.

The structural components of the shape memory polymer coil 100 having been described and illustrated in FIG. 1, the construction and operation of the shape memory polymer coil 100 will now be described. The shape memory polymer coil 100 provides a mechanical device, to be attached to a transport vehicle and delivered via a catheter, to remove non-vascular or vascular occlusions (e.g., blood clot) from the body. The shape memory polymer coil 100 dimensions depend on the size and location of the occlusion targeted for removal (e.g., a device used to remove a carotid artery occlusion may be larger than a device used to remove an occlusion located further up in the neurovasculature). The shape memory polymer coil 100 is shown in its expanded form in FIG. 1. The shape memory polymer coil 100 is initially in its collapsed secondary straight form as the shape memory polymer coil 100 is pushed distally through the occlusion. With the coil body 102 positioned distal to the occlusion, the coil is thermally actuated into its expanded primary forms by heating above the soft phase glass transition temperature of the SMP. The expanded shape memory polymer coil 100 is retracted until the occlusion is captured. The expanded shape memory polymer coil 100 and the captured occlusion are withdrawn from the body.

Various incarnations of the shape memory polymer coil 100 are possible depending on the actuation mechanism. Actuation mechanisms include laser heating, resistive heating, inductive heating, heated fluid injection and heating by ambient (physiological) temperature. Additionally, the shape memory polymer coil 100 may actuate at physiological temperature through a depression in the SMP glass transition temperature caused by exposure to physiological fluids or those injected through the catheter. Though the design and construction of the shape memory polymer coil 100 are specific to the actuation mechanism, the various incarnations of the devices are functionally identical.

Figure 2:
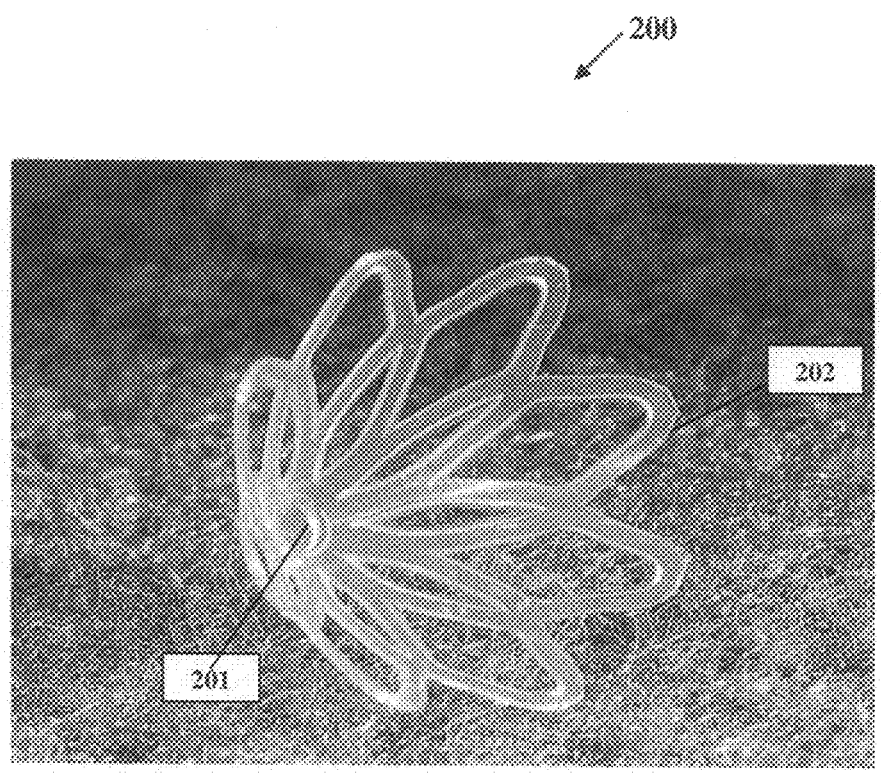
FIG. 2 is an illustration of a shape memory polymer basket of one embodiment of an actuator for acting upon a material in a vessel of the present invention.

Referring now to the drawings and in particular to FIG. 2, an illustration of a shape memory polymer basket of one embodiment of an actuator for acting upon a material in a vessel of the present invention is shown. The shape memory polymer basket of this embodiment is designated generally by the reference numeral 200. The shape memory polymer basket 200 includes the following structural components: an attachment portion 201 and an expandable basket portion 202. The attachment portion 201 of the shape memory polymer basket 200 is adapted to be connected to the distal end of a catheter and attached to the catheter. This catheter is also used to deliver the shape memory polymer coil. The shape memory polymer basket 200 comprises a shape memory polymer (SMP), a polymer that can be formed into a primary or equilibrium shape, re-formed into a stable secondary or stressed shape, and actuated by controlled heating to recover its primary shape.

The structural components of the shape memory polymer basket 200 having been described and illustrated in FIG. 2, the construction and operation of the shape memory polymer basket 200 will now be described. The shape memory polymer basket 200 provides a mechanical device, to be situated at the distal end of a catheter, to remove non-vascular or vascular occlusions (e.g., blood clot) from the body. The shape memory polymer basket 200 dimensions depend on the size and location of the occlusion targeted for removal (e.g., a device used to remove a carotid artery occlusion may be larger than a device used to remove an occlusion located further up in the neurovasculature). The shape memory polymer basket 200 is shown in its expanded form in FIG. 2. The shape memory polymer basket 200 is situated at the distal end of a catheter. The shape memory polymer basket 200 is initially in its collapsed secondary form as the shape memory polymer basket 200 moved until it is near the occlusion. With the basket body 202 positioned near the occlusion, the basket is thermally actuated into its expanded primary form by heating above the soft phase glass transition temperature of the SMP. The transport vehicle with the attached expanded shape memory polymer coil 100 is retracted through the catheter until the occlusion is wedged against the expandable basket portion 202 to capture the occlusion. The expanded shape memory polymer basket 200, the expanded shape memory polymer coil 100, and the captured occlusion are withdrawn from the body.

Various incarnations of the shape memory polymer basket 200 are possible depending on the actuation mechanism. Actuation mechanisms include laser heating, resistive heating, inductive heating, heated saline flush and heating by ambient (physiological) temperature. Additionally, the shape memory polymer basket 200 may actuate at physiological temperature through a depression in the SMP Tg caused by exposure to physiological fluids or those injected through the catheter. Though the design and construction of the shape memory polymer basket 200 are specific to the actuation mechanism, the various incarnations of the devices are functionally identical.

Figure 3:
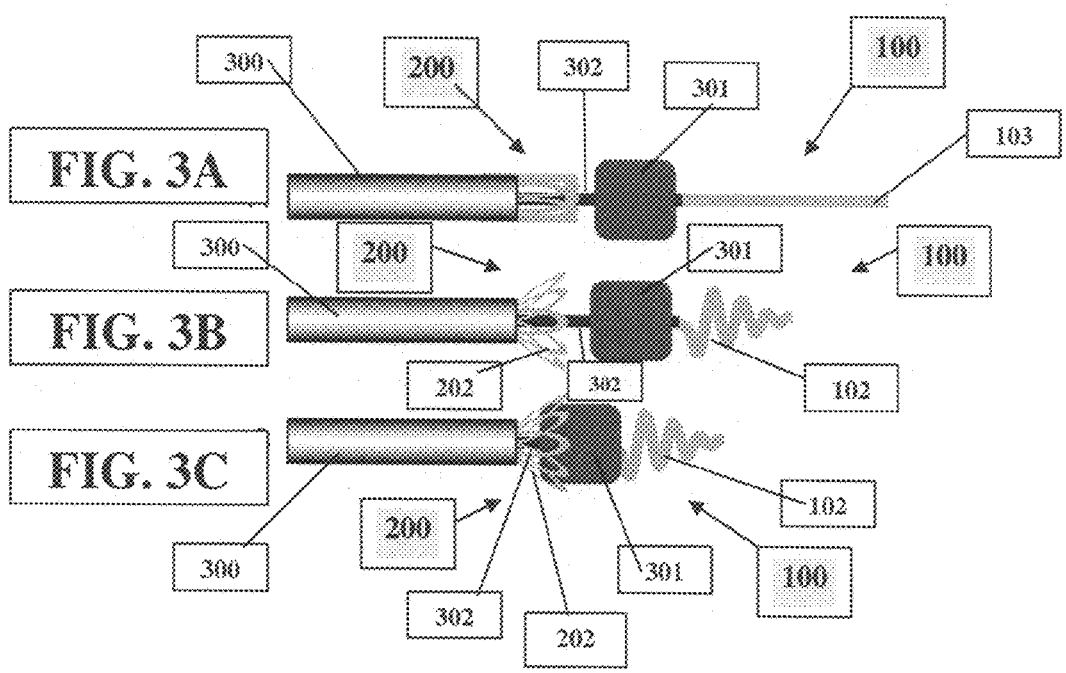
FIGS. 3A, 3B, and 3C are a series of three diagrams illustrating principles of operation of the shape memory polymer expandable coil and the shape memory polymer basket of an actuator for acting upon a material in a vessel of the present invention.

Referring now to the drawings and in particular to FIG. 3A, FIG. 3B, and FIG. 3C, a series of three diagrams are shown illustrating principles of operation of the shape memory polymer expandable coil 100 and the shape memory polymer basket 200. The shape memory polymer expandable coil 100 is attached to a transport vehicle 302 and pushed through a catheter 300. The shape memory polymer basket 200 is situated at the distal end of a catheter 300. Uses of the present shape memory polymer expandable coil 100 and the shape memory polymer basket 200 include, but are not limited to, the removal of obstructions from vascular or non-vascular passageways in the body. Such occlusions may include a thrombus (clot), plaque, fatty deposits, and other natural materials as well as fragments of man made devices. An example of an application is blood clot removal following ischemic stroke.

Referring now to FIG. 3A, both the shape memory polymer expandable coil 100 and the shape memory polymer basket 200 are initially in their collapsed secondary forms as the device is pushed distally through an occlusion 301. The distal end 103 of the shape memory polymer coil 100 passes through the occlusion 301. The coil corkscrew body 102 of the shape memory polymer coil 100 is also moved through the occlusion 301.

Referring now to FIG. 3B, with the shape memory polymer expandable coil 100 positioned distal to the occlusion 301 and the shape memory polymer basket 200 proximal to the occlusion 301, the coil 100 and basket 200 are thermally actuated into their expanded primary forms by heating above the soft phase glass transition temperature of the SMP. The expandable basket portion 202 opens and is in position to receive the occlusion 301.

Referring now to FIG. 3C, the expanded coil 100 is retracted until the occlusion 301 is wedged against the expanded basket 202. Note that the coil 100, which is attached to the transport vehicle 302, moves independently of the basket 200, which is connected to the catheter 300. Finally, the entire catheter assembly, including the captured occlusion 301, is withdrawn from the body.

Various designs of the system using either the SMP coil 100 or the SMP basket 200 or the SMP coil 100 and the SMP basket 200 are possible. For example, a coil design using inductive heating actuation will be described. Ferromagnetic particles are embedded in thermosetting SMP material by mixing the particles into the SMP material prior to curing or embedded in thermoplastic SMP material through melt compounding followed by extrusion of strand. The uncured thermosetting SMP is then injection-molded directly into the "corkscrew" shape (using a 3-dimensional mold) or straight rod shape, in which case it is subsequently wrapped around a conical mandrel and heated to set the primary "corkscrew" shape. The SMP coil is mounted on the distal end of a guide wire (transport vehicle) long enough to extend through the catheter up to the occlusion. Actuation into the expanded coil form is achieved by subjecting the device to an externally generated alternating magnetic field, resulting in inductive heating of the magnetic particles. The type, size, and concentration of magnetic particles and the strength of the external magnetic field govern the heating response. No physical connection between the device and energy source is required.

A coil design using actuation through SMP adsorption of plasticizing material will be described. In this embodiment the SMP coil is mounted on a guide wire which may be a standard guide wire. In this embodiment the SMP material, which may be thermoplastic or thermoset, has a glass transition temperature that is initially higher than physiological temperature, but is depressed below physiological temperature by the adsorption of a plasticizing material, which may either be injected into the vicinity of the SMP coil through the catheter or derived from the surrounding physiological fluid. Examples of potentially plasticizing compounds are water, ethanol, and dimethyl sulfoxide. The time period between the insertion of the device into the physiology and the device actuation can be controlled; this being done for example by the time at which it is exposed to externally injected plasticizer, the use of a coating on the surface of the coil which controls the diffusion rate of plasticizer into the coil geometry and initial barrier which provides for a lag time, or the coating of the device with a material which can be controllably removed by dissolution in turn allowing for the adsorption of the plasticizer.

A coil design using actuation of SMP by equilibration to physiological temperature will be described. In this embodiment the SMP coil is mounted on a guide wire which may be a standard guide wire. In this embodiment the SMP material, which may be thermoplastic or thermoset, has a glass transition temperature that is close to physiological temperature. The SMP glass transition temperature is chosen such that the SMP coil can be delivered to through the site of the occlusion prior to the SMP reaching physiological temperature and having time kinetically to recovery its primary shape. Once placed, the SMP coil will spontaneously actuate into the coil form over time and can then be used to remove the occlusion. The kinetic hindering of the SMP coil actuation is achieved by one or more of the following methods: kinetic slowing of the heating of the SMP coil device while it remains in the catheter, coating of the SMP coil device with an elastomer (e.g., PDMS) which acts as an insulating barrier, and/or use of an SMP which has a glass transition temperature slightly above physiological temperature but which is still low enough for actuation to occur at physiological temperature. It should be noted that this mechanism is easily combined with adsorption of plasticizing material described previously to further enhance control over actuation kinetics.

A basket design using inductive heating actuation will be described. Ferromagnetic particles are embedded in the thermosetting SMP material by mixing the particles into the uncured liquid SMP material prior to injection molding. The basket is mounted to the distal end of the catheter using epoxy or by other suitable means. Actuation into the "open basket" form is achieved by subjecting the device to an externally generated alternating magnetic field, resulting in inductive heating of the magnetic particles. The type, size, and concentration of magnetic particles and the strength of the external magnetic field govern the heating response. No physical connection between the device and energy source is required.

A basket design using resistive heating actuation (Hot Catheter Tip) will be described. An electrical heating element is placed at the distal end of the catheter to which the SMP basket is mounted. The element may serve as an extension of the catheter with the SMP basket attached directly to the element. Leads running from a power supply (external to the body) extend along the catheter (through lumens in the catheter wall) and are connected to the terminals of the resistive element. Actuation into the expanded coil form is achieved by applying a voltage to drive a current through the resistive element, causing it to heat the SMP above its transition temperature.

A basket design using actuation through glass transition temperature depression with exposure of the SMP basket to plasticizing fluid will be described. The SMP basket may be caused to expand by various mechanisms. For example, the SMP basket may be exposed to and allowed to absorb a plasticizing material which depresses the SMP glass transition and allows actuation, the SMP basket may be made of an SMP with a glass transition close to physiological temperature so that actuation will occur over time once the device has reached that temperature from its initial lower temperature, or the two preceding two methods may be used together to control the kinetics of the SMP basket opening. It should be noted that in this embodiment actuation can be achieved at a controlled time without application of energy to the device.

A basket design using resistive heating with direct resistive heating of the basket will be described. The SMP basket has a conductive element embedded within the SMP. The element may be a resistive wire or conductive polymer composite. Leads running from a power supply (external to the body) extend along the catheter (through lumens in the catheter wall) and are connected to the terminals of the resistive element. Actuation into the expanded basket form is achieved by applying a voltage to drive a current through the resistive element, causing it to heat the SMP above its transition temperature.

Figure 4:
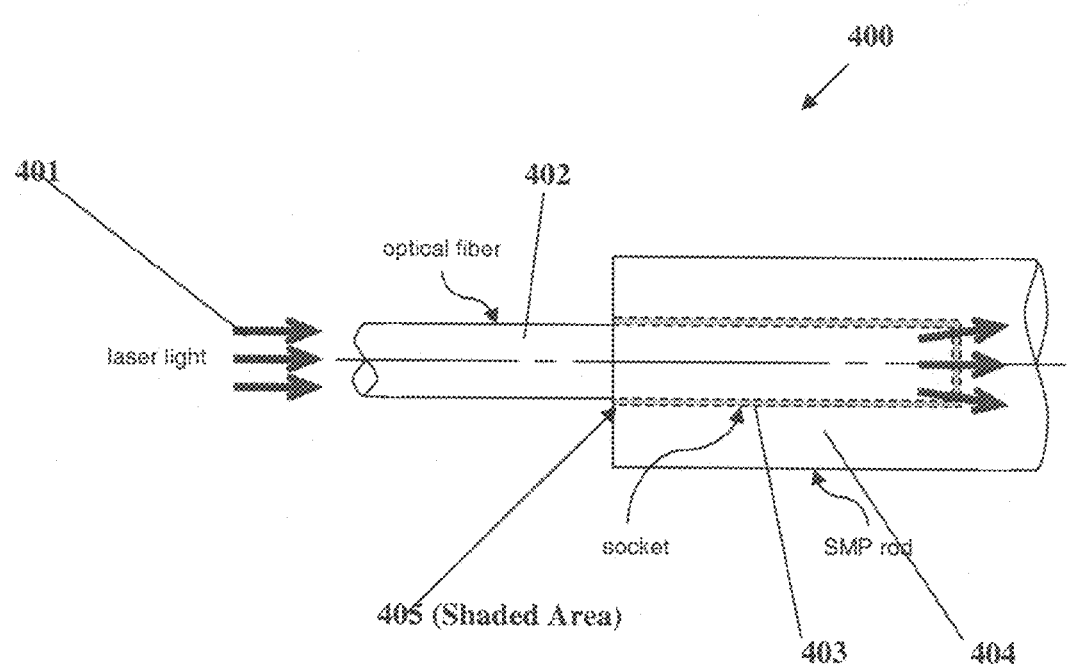
FIG. 4 is an illustration of a SMP-fiber socket joint of one embodiment of an actuator for acting upon a material in a vessel of the present invention.

Referring now to FIG. 4, an illustration of a SMP-fiber socket joint for laser heating of the SMP coil of one embodiment of an actuator for acting upon a material in a vessel of the present invention is shown. The SMP-fiber socket joint of this embodiment is designated generally by the reference numeral 400. The SMP-fiber socket joint 400 includes the following structural components: optical fiber 402, coaxial socket 403, SMP rod 404, and optically transparent index-matched epoxy 405. The optical fiber 402 is bonded in place with an optically transparent index-matched epoxy 405 (shaded area). The socket joint 400 provides a large bonding surface area for increased joint strength and the index-matched epoxy maximizes optical transmission.

The structural components of a SMP-fiber socket joint 400 of one embodiment of an actuator for acting upon a material in a vessel of the present invention having been described and illustrated in FIG. 4, the construction and operation of the SMP-fiber socket joint 400 will now be described. Raw thermoplastic SMP pellet material is extruded into a strand with circular cross-section and a cylindrical rod segment is obtained. The radius and length of the rod 404 are chosen to form a device of the desired size depending on the location of the occlusion. If the SMP itself does not significantly absorb the laser light and, hence, is not sufficiently heated by the laser light to achieve primary shape recovery, laser-absorbing dye may be added to the SMP. The raw pellets may be doped with laser-absorbing dye prior to extrusion to enhance laser heating, yielding a uniformly doped SMP strand. Alternatively, the SMP rod may be soaked in a solvent (e.g., methanol) containing the dissolved dye, allowing the dye to migrate into the SMP, and subsequently vacuum dried to remove the solvent; this method permits introduction of dye concentration gradients (radial and/or axial) in the rod to optimize laser penetration for uniform heating along the rod length.

In addition to soaking in a solution of solvent and dye or doping the uncured SMP with dye, dye may be incorporated into the devices by dipcoating in a solution consisting of dye and SMP dissolved in a solvent and then vacuum dried to remove the solvent. This process yields a device in which the dye is localized in an outer layer. In the case of the SMP coil device, this process results in more uniform axial heating of the device due to increased laser light penetration depth. A dye concentration gradient may be imparted by varying the dipcoating speed to further enhance the uniformity of heating.

In one end of the rod 404, a socket 403 is created (by mechanical or laser drilling or other means) along the longitudinal axis of the rod 404. The hole is partially filled with an optically transparent epoxy 405 whose index of refraction is chosen to maximize transmission of laser light into the SMP. The cleaved end of a glass or plastic optical fiber 402 is inserted into the hole 403 and bonded in place, being careful that any space between the cleaved end of the optical fiber 402 and the SMP surface is filled with the index-matched epoxy 405. The other end of the optical fiber 402 is coupled to a laser. The optical fiber 402 must be long enough to extend from the laser (outside the body), through a catheter to the occlusion (inside the body).

Referring again to FIG. 4, the configuration of the SMP-fiber joint 400 is illustrated. The cleaved end of the optical fiber 402 is inserted into a coaxial socket 403 in the SMP rod 404 and bonded in place with epoxy 405. Laser light 401 is transmitted through the optical fiber 402, emerging at the distal end of the fiber 402 and continuing to propagate axially along the SMP 404. The socket joint 400 provides a large bonding surface area for increased strength and the index-matched epoxy maximizes optical transmission.

The SMP rod 404, with the optical fiber 402 attached, is wrapped around a conical mandrel and heated above its highest glass transition temperature to set the primary "corkscrew" shape as illustrated in FIG. 1 (i.e., the expanded form of the SMP coil). A narrow channel machined around the mandrel and a cap placed over the mandrel hold the wrapped SMP rod in place during the heating procedure.

Figure 5:
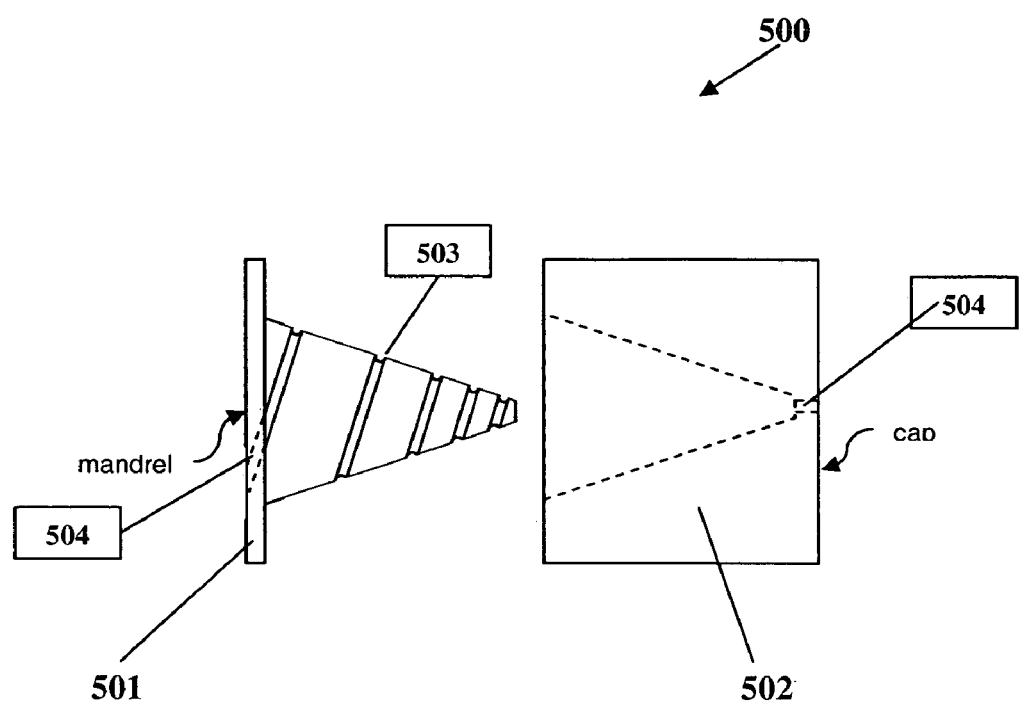
FIG. 5 shows a mandrel system used to set the primary "corkscrew" shape of the SMP coil.

Referring now to FIG. 5, a mandrel system used to set the primary "corkscrew" shape of the SMP coil is illustrated. The mandrel system is designated generally by the reference numeral 500. The SMP rod is wrapped around the conical mandrel 501 in the provided channel 503 and held in place by the overlying cap 502 during heating. Exits ports 504 are located on the mandrel 501 and cap 502 through which the ends of the SMP protrude during heating.

The structural components of a mandrel system 500 of one embodiment of an actuator for acting upon a material in a vessel of the present invention having been described and illustrated in FIG. 5, the construction and operation of the mandrel system 500 will now be described. The SMP rod, with the optical fiber attached, is wrapped around the conical mandrel 501 and heated above its highest glass transition temperature to set the primary "corkscrew" shape (i.e., the expanded form of the SMP coil). A narrow channel 503 machined around the mandrel 501 and a cap 502 placed over the mandrel 501 hold the wrapped SMP rod in place during the heating procedure. An example of the mandrel is shown in FIG. 5. After removing the SMP coil (now in its primary expanded shape) from the mandrel 501, the SMP coil is manually straightened while heated slightly above its soft phase glass transition temperature to set its secondary "rod" form prior to use. Additionally the "corkscrew" shape can be set by inserting the rod into a flexible tube, attaching the tube to a guide, such as a wire, and forming the guide, tube, and SMP into the "corkscrew" shape. The apparatus is then heated to above the highest glass transition temperature and allowed to cool, thereby setting the primary shape.

Uncured thermosetting SMP material can be cast into the primary "corkscrew" shape by injection-molding using a 3-dimensional mold, consisting, for example, of flexible PTFE tubing held in the desired shape, or a complex metal mold. These methods automatically set the primary shape. If injection-molded into a straight rod shape, the SMP can be re-set into the primary shape (using the same methods as the thermoplastic SMP). Laser-absorbing dye may be incorporated into the SMP by doping the uncured material prior to molding, by soaking the cured material in a solvent in which the dye is dissolved followed by vacuum drying, or by dip-coating in a solution consisting of dye and SMP dissolved in a solvent and then vacuum dried to remove the solvent, as described above. The socket to receive the optical fiber may be created by drilling, as described above, or may be incorporated into the mold. Alternatively, the optical fiber may be inserted into the SMP as it cures in the mold. In this case, the application of index-matched epoxy in the socket is not necessary. However, epoxy may be used to reinforce the bond externally. The SMP coil is manually straightened while heated slightly above its soft phase glass transition temperature to set its secondary "rod" form prior to use.

The smooth "corkscrew" shape and circular cross-section of the SMP permit the laser light to propagate along the SMP coil while providing a means of capturing an occlusion. In order for the SMP rod to behave as a light guide, the conditions for total internal reflection must be satisfied. These conditions force the index of refraction of the SMP to exceed that of its surrounding medium (e.g., blood or other body fluid) and put a lower limit on the coil turn radius established by the mandrel. Departure from these conditions will result in excessive leakage of the laser light from the SMP rod and incomplete expansion of the SMP coil. The SMP coil may be thinly coated with a material with a sufficiently low index of refraction (e.g., PDMS) to ensure light transmission regardless of the surrounding medium. However, the mechanical properties of the coating must not impede expansion of the SMP coil during laser heating. Though some of the laser light is reflected back from the distal end of the SMP coil due to the index mismatch, this effect may be augmented by making the distal end of the SMP coil reflective (e.g., coated with silver or gold) to enhance the laser heating by recapturing laser light that would otherwise escape.

Figure 6:
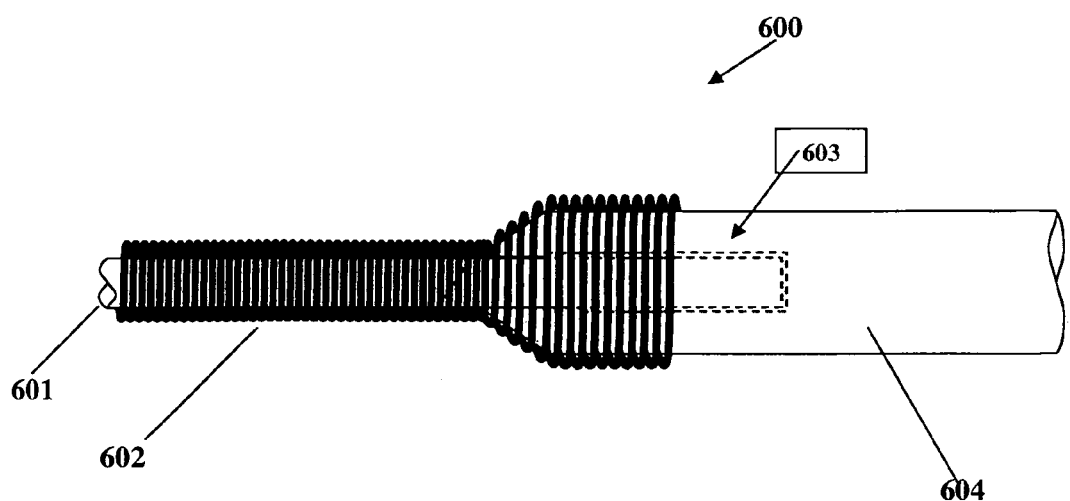
FIG. 6 shows a wire-wrapped optical fiber with attached SMP expandable coil.

Referring now to FIG. 6, a wire-wrapped optical fiber 601 with attached SMP expandable coil 604 is illustrated. The overall system is designated generally by the reference numeral 600. The wire windings 602 encompass the entire optical fiber 601, comprising the transport vehicle, and are shown slightly overlapping the SMP expandable coil 604 in the vicinity of the SMP-fiber joint 603. The wire windings 602 are secured to the optical fiber 601 and SMP 604 using epoxy or other suitable means such that the wire windings and optical fiber-SMP assembly move as a single unit.

The structural components of a wire-wrapped optical fiber 601 with attached SMP expandable coil 604 of one embodiment of an actuator for acting upon a material in a vessel of the present invention having been described and illustrated in FIG. 6, the construction and operation of the wire-wrapped optical fiber 601 with attached SMP expandable coil 604 will now be described. The SMP expandable coil system 600 is typically delivered to the desired location via a catheter. Wire windings 602 will encompass the optical fiber 601, extending from the proximal (laser) end to the distal (coil) end, providing the strength and torqueability necessary to push the SMP expandable coil up to and through the occlusion and to retract the device. The stiffness of the windings may vary along the length of the fiber to enhance maneuverability (stiffer at proximal end, more flexible at distal end).

Figure 7:
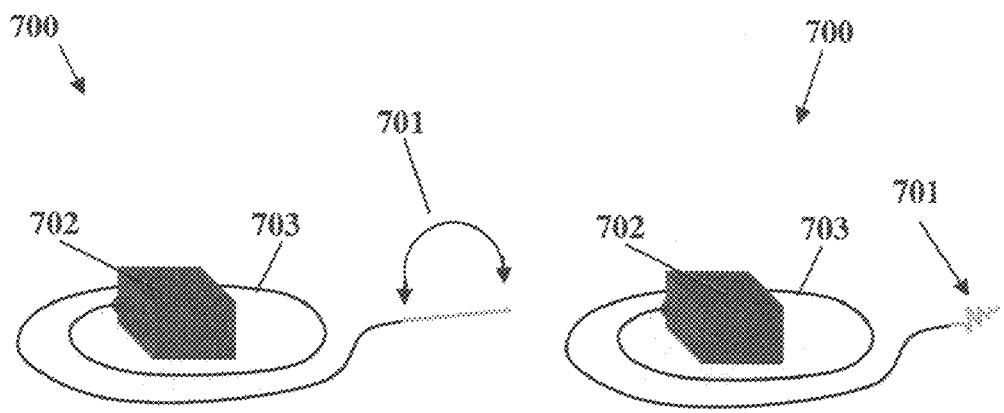
FIGS. 7A and 7B show a wire-wrapped optical fiber with attached SMP expandable coil that comprises an expandable coil device.

Referring now to FIG. 7A and FIG. 7B, a wire-wrapped optical fiber with attached SMP expandable coil that comprises an expandable coil device is illustrated. The expandable coil device is designated generally by the reference numeral 700. A SMP expandable coil 701 is connected to the laser actuation source 702 via an optical fiber 703. The expandable coil device 700 is shown in its pre-actuation collapsed form in FIG. 7A. The expandable coil device 700 is shown in its post-actuation expanded "corkscrew" form in FIG. 7B. The SMP coil 701 is mounted on the distal end of the optical fiber 703 which is coupled to the laser 702.

The SMP expandable coil 701 is typically delivered to the desired location via a catheter. Wire windings will encompass the optical fiber, extending from the proximal (laser) end to the distal (coil) end, providing the strength and torqueability necessary to push the SMP expandable coil up to and through the occlusion and to retract the device. The stiffness of the windings may vary along the length of the fiber to enhance maneuverability (stiffer at proximal end, more flexible at distal end).

Figure 8:
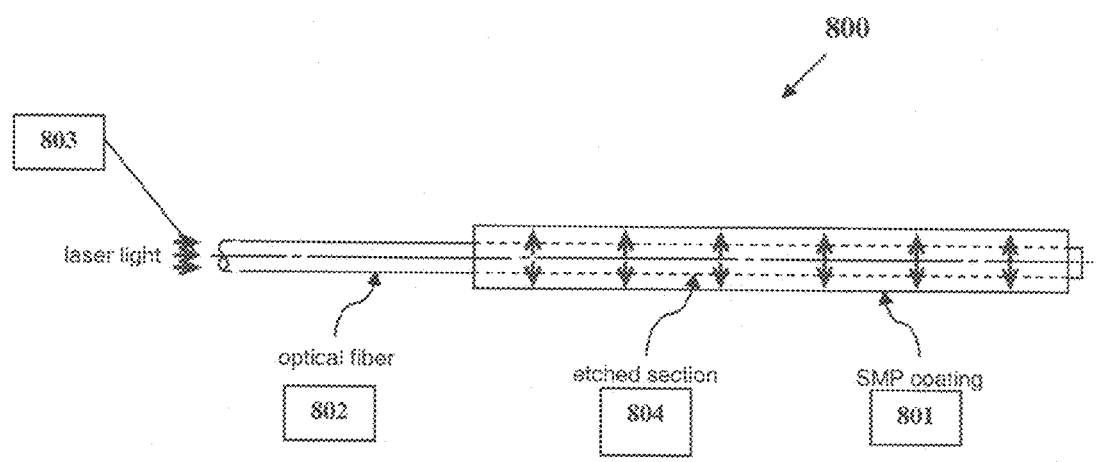
FIG. 8 is an illustration of a shape memory polymer coil mounted on a radially diffusing optical fiber of one embodiment of an actuator for acting upon a material in a vessel of the present invention.

Referring now to FIG. 8, an illustration of a shape memory polymer coil mounted on a radially diffusing optical fiber for laser heating of one embodiment of an actuator for acting upon a material in a vessel of the present invention is shown. The shape memory polymer coil mounted on a radially diffusing optical fiber of this embodiment is designated generally by the reference numeral 800. The shape memory polymer coil mounted on a radially diffusing optical fiber 800 includes the following structural components: a coating of SMP material 801 (a coil shown in its straight form), a radially diffusing optical fiber 802, and an etched section 804.

The structural components of the shape memory polymer coil mounted on a radially diffusing optical fiber 800 having been described and illustrated in FIG. 8, the construction and operation of the shape memory polymer coil mounted on a radially diffusing optical fiber 800 will now be described. The layer of SMP 801 is applied over the etched (diffusing) section 804 of the optical fiber 802. The laser light 803 propagates radially outward into the SMP to induce actuation. The shape memory polymer coil mounted on a radially diffusing optical fiber 800 uses an optical fiber, possibly encompassed with wire windings, comprising the transport vehicle, with the SMP coil located near the distal end of the fiber. However, rather than joining the SMP coil to the distal tip of the fiber, a section of the fiber is coated with SMP material 801; this coated section is formed into the expandable coil. A section 804 of optical fiber 802, approximately equal in length to the SMP coil in its straight form, is made to be radially diffusing by chemically or mechanically etching the fiber surface. This section 804 is coated with thermosetting or thermoplastic SMP which may be doped with laser-absorbing dye. The coated section is wrapped around the conical mandrel and heated to set the primary coil form. The thickness of the SMP layer must be sufficient to coerce the encompassed optical fiber into the expanded coil form upon actuation. If the layer is too thin, the shape recovery force will not overcome the fiber stiffness. As laser light 803 propagates along the fiber 802, it will leak radially where the fiber surface has been etched in section 804, propagating into the SMP layer 801 to induce actuation to the coil form.

Figure 9:
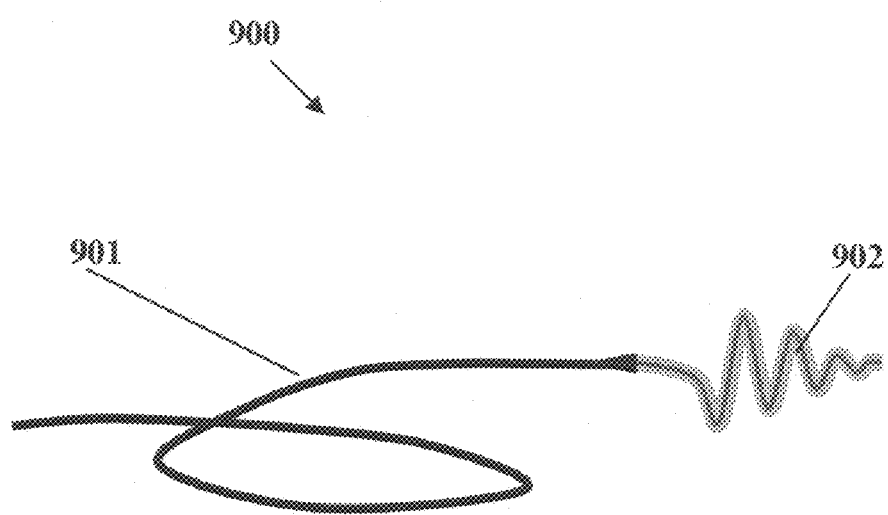
FIG. 9 is an illustration of an extruded strand of thermoplastic SMP of one embodiment of an actuator for acting upon a material in a vessel of the present invention.

Referring now to FIG. 9, an illustration of an extruded strand of thermoplastic SMP using laser heating actuation of one embodiment of an actuator for acting upon a material in a vessel of the present invention is shown. The extruded strand of thermoplastic SMP of this embodiment is designated generally by the reference numeral 900. The extruded strand of thermoplastic SMP 900 includes the following structural components: an extruded strand of thermoplastic SMP 901 and a coil 902 of a primary "corkscrew" form at the distal end of the extruded strand.

The structural components of the extruded strand of thermoplastic SMP 900 having been described and illustrated in FIG. 9, the construction and operation of the extruded strand of thermoplastic SMP 900 will now be described. The extruded strand of thermoplastic SMP 900 is of a circular cross-section and is long enough to extend from a laser or from an intermediate optical fiber coupled to a laser (outside the body), through a catheter to the occlusion (inside the body). The extruded strand of thermoplastic SMP 900 is coupled to the laser at the proximal end. The laser light travels down the SMP strand where it is absorbed by the dye-doped shape memory section at the distal end. The distal portion of the strand (length equivalent to that of the straightened coil) is doped with laser-absorbing dye by soaking in a solvent with dissolved dye or by dipcoating in a solution consisting of dye and SMP dissolved in a solvent and then vacuum drying (uniform or graded dye concentration). This portion is wrapped around the conical mandrel and heated to set the primary "corkscrew" form. The laser light is transmitted along the SMP strand distally to the shape memory region where the light is absorbed and the coil 902 is actuated. The SMP strand may be coated with a material with a lower index of refraction (e.g., PDMS) to enhance its light guiding efficiency, and it may be encompassed with wire windings up to the distal coil portion.

Figure 10:
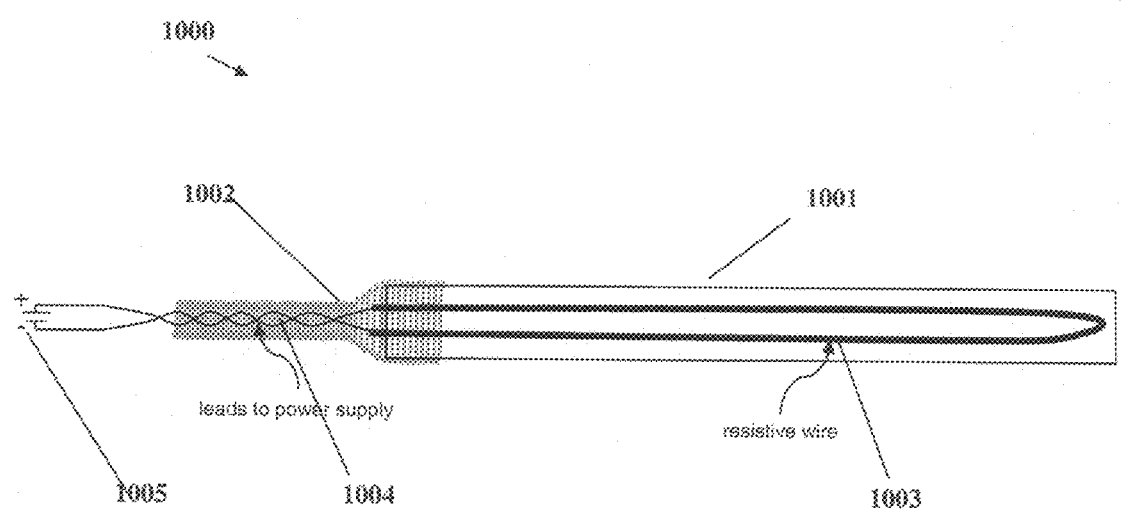
FIG. 10 is an illustration of a coil design having resistive heating actuation of one embodiment of an actuator for acting upon a material in a vessel of the present invention.

Referring now to FIG. 10, an illustration of a coil design having resistive heating actuation of one embodiment of an actuator for acting upon a material in a vessel of the present invention is shown. The coil design having resistive heating actuation of this embodiment is designated generally by the reference numeral 1000. The coil design having resistive heating actuation 1000 includes the following structural components: a shape memory material 1001, a guide wire 1002, a flexible, resistive element 1003, leads 1004, and a power source 1005.

The structural components of the coil design having resistive heating actuation 1000 having been described and illustrated in FIG. 10, the construction and operation of the coil design having resistive heating actuation 1000 will now be described. The SMP coil 1001 is shown in its secondary straight form attached to a guide wire 1002 (wire windings). It contains a resistive heating element 1003 such as a metal wire loop. The terminals of the wire extend beyond the proximal end of the SMP rod and are connected to leads 1004 running through the guide wire that is connected to the power supply 1005.

A flexible, resistive element 1003 (e.g., loop of NiCr wire or flexible graphite) is coated with or embedded in the thermosetting or thermoplastic SMP 1001. The resistive element 1003 may be coated with the SMP 1001 using various techniques (e.g., dip-coating or powder deposition) or embedded into the SMP 1001 during an injection-molding process or by co-extrusion. The thickness of the overlying SMP 1001 must be sufficient to coerce the encompassed resistive element 1003 into the expanded coil form upon actuation. The SMP 1001 containing the resistive element 1003 is wrapped around a conical mandrel and heated to set the primary "corkscrew" shape. The SMP coil 1001 is mounted on the distal end of a guide wire 1002 long enough to extend through the catheter up to the occlusion. Leads 1004 running from a power supply 1005 (external to the body) extend through the guidewire 1002 and are connected to the exposed terminals of the resistive element 1003 at the proximal end of the SMP 1001. Actuation into the expanded coil form is achieved by applying a voltage to drive a current through the resistive element 1003, causing it to heat the SMP 1001 above its transition temperature.

Figure 11A:
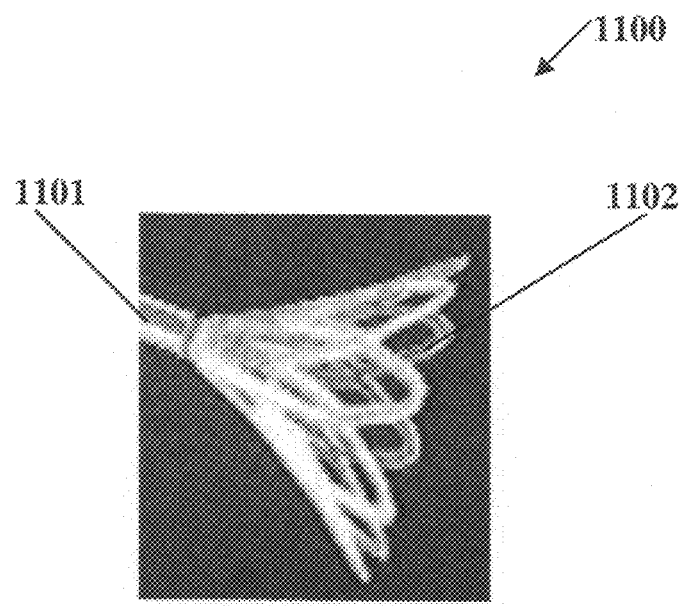
FIGS. 11A and 11B provide an illustration of a SMP basket of one embodiment of an actuator for acting upon a material in a vessel of the present invention.
Figure 11B:
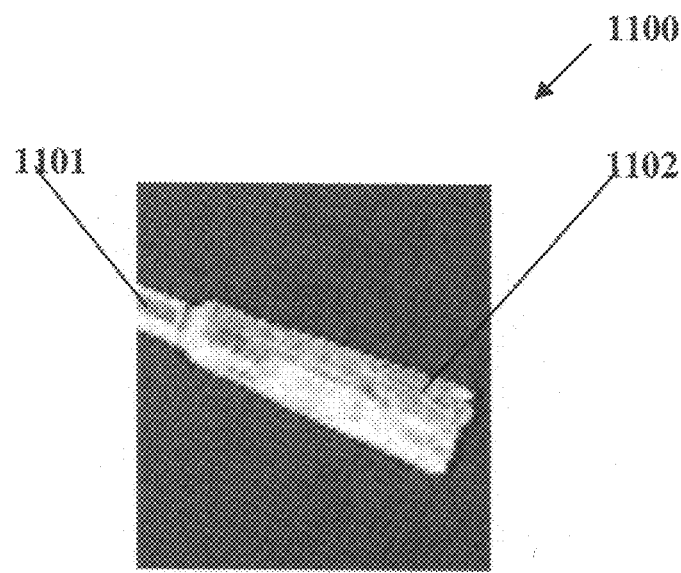

Referring now to FIG. 11A and FIG. 11B, an illustration of a SMP basket of one embodiment of an actuator for acting upon a material in a vessel of the present invention is shown. The SMP basket of this embodiment is designated generally by the reference numeral 1100. The SMP basket 1100 includes the following structural components: an attachment portion 1101 and an expandable basket portion 1102. The attachment portion 1101 of the shape memory polymer basket 1100 is adapted to be connected to the distal end of a catheter and attached to the catheter. The shape memory polymer basket 1100 comprises a shape memory polymer (SMP), a polymer that can be formed into a primary or equilibrium shape, re-formed into a stable secondary or stressed shape, and actuated by controlled heating to recover its primary shape.

The structural components of the SMP basket 1100 having been described and illustrated in FIG. 11, the construction and operation of the SMP basket 1100 will now be described. The SMP expandable basket 1100 may be coupled with any of the SMP coil designs described herein to complete the occlusion removal device. The basic basket fabrication process is the same for the actuation mechanisms (laser, resistive, or inductive heating, heated saline flush, or ambient (physiological) heating). The fabrication process of the SMP basket 1100 is described below, followed by device incarnations for the various actuation mechanisms. The actuation mechanism may coincide with that of the SMP expandable coil (e.g., inductive heating of both the coil and the basket) or may be completely independent (e.g., inductive heating of the basket and laser heating of the coil). In all cases, the SMP basket is mounted to the distal tip of the catheter through which the SMP expandable coil device is delivered.

The SMP basket is designed in a way that allows it to be heated and reformed or consolidated from its primary "open basket" shape shown in FIG. 11A into a secondary tubular shape shown in FIG. 11B that initially acts as a distal extension of the catheter. Each web of the basket 1102 has a designed width that when consolidated into a tube forms a solid wall. Upon heating above its transition temperature, the SMP basket expands to recover its primary "open basket" form shown in FIG. 11A. The device is shown in its pre-actuation collapsed form in FIG. 11B.

Figure 12:
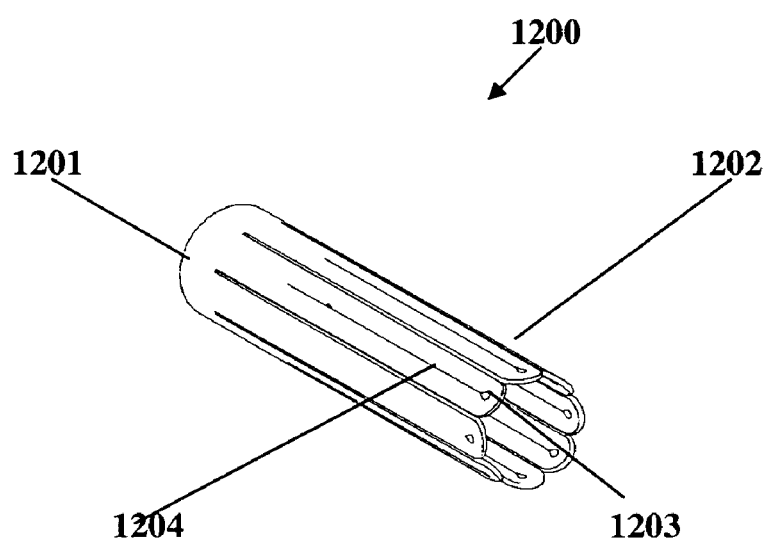
FIG. 12 is an illustration of another embodiment of a SMP basket of an actuator for acting upon a material in a vessel.

Referring now to FIG. 12, an illustration of another embodiment of a SMP basket of an actuator for acting upon a material in a vessel of the present invention is shown. The SMP basket of this embodiment is designated generally by the reference numeral 1200. The SMP basket 1200 includes the following structural components: an attachment portion 1201 and an expandable basket portion 1202. The attachment portion 1201 of the shape memory polymer basket 1200 is adapted to be connected to the distal end of a catheter and attached to the catheter. The shape memory polymer basket 1200 comprises a shape memory polymer (SMP), a polymer that can be formed into a primary or equilibrium shape, re-formed into a stable secondary or stressed shape, and actuated by controlled heating to recover its primary shape. The expandable basket portion 1202 has leaves 1203 with slits 1204.

The structural components of the SMP basket 1200 having been described and illustrated in FIG. 12, the construction and operation of the SMP basket 1200 will now be described. The SMP expandable basket 1200 may be coupled with any of the SMP coil designs described herein to complete the occlusion removal device. The basic basket fabrication process is the same for the actuation mechanisms (laser, resistive, or inductive heating, heated saline flush, or ambient (physiological) heating).

The SMP basket is designed in a way that allows it to be heated and reformed or consolidated from its primary "open basket" shape into a secondary tubular shape shown in FIG. 12 that initially acts as a distal extension of the catheter. Each web of the basket has leaves 1203 with slits 1204 and has a designed width that when consolidated into a tube forms a solid wall. Upon heating above its transition temperature, the SMP basket expands to recover its primary "open basket" form. The device is shown in its pre-actuation collapsed form in FIG. 12.

The first step in the fabrication of the SMP basket is to mold the basket structure as a two-dimensional part. The mold is fabricated by chemically etching or machining the grooves that will form the structure into a flat plate. This mold plate is then clamped between two ridged plates to form the completed mold. There is a port in the center of one of the outside plates to allow the injection of the uncured thermosetting SMP. The filled mold is allowed to rest at room temperature temporarily and then heated to accelerate curing of the SMP. Injection molding a thermoplastic SMP is also feasible.

Figure 13A:
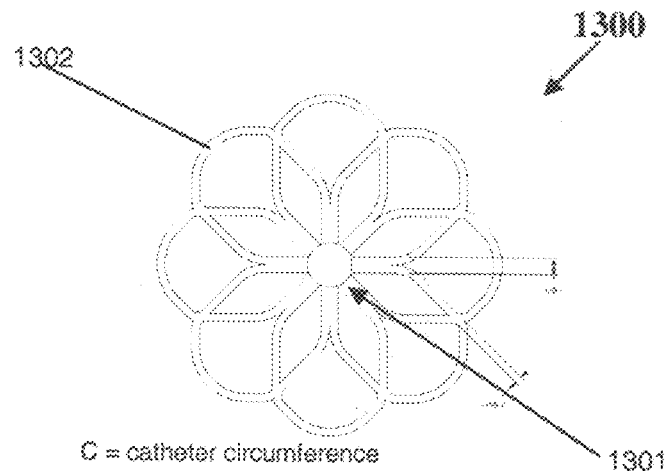
FIGS. 13A and 13B provide an illustration of another embodiment of a SMP basket of an actuator for acting upon a material in a vessel.
Figure 13B:
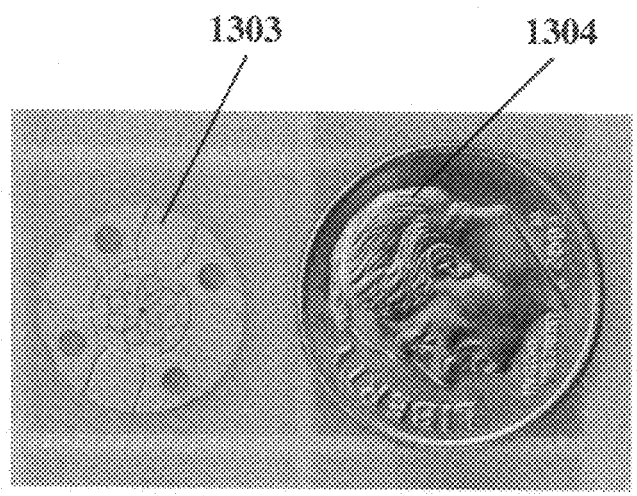

Referring now to FIG. 13A and FIG. 13B, an illustration of another embodiment of a SMP basket of an actuator for acting upon a material in a vessel of the present invention is shown. The SMP basket of this embodiment is designated generally by the reference numeral 1300. The SMP basket 1300 of this embodiment representing the two-dimensional (as molded) part shown in FIG. 13A includes the following structural components: a SMP basket attachment portion 1301 and a SMP expandable basket portion 1302. The SMP basket 1300 of this embodiment shown in FIG. 13B includes the following structural components: a mold plate 1303 with grooves for casting the two-dimensional basket. The attachment portion 1301 of the shape memory polymer basket 1300 is adapted to be connected to the distal end of the catheter and attached to the catheter. The shape memory polymer basket 1300 comprises a shape memory polymer (SMP), a polymer that can be formed into a primary or equilibrium shape, re-formed into a stable secondary or stressed shape, and actuated by controlled heating to recover its primary shape.

The structural components of the SMP basket 1300 having been described and illustrated in FIGS. 13A and 13B, the construction and operation of the SMP basket 1300 will now be described. The SMP expandable basket 1300 may be coupled with any of the SMP coil designs described herein to complete the occlusion removal device. The basic basket fabrication process is the same for the actuation mechanisms (laser, resistive, or inductive heating, heated saline flush, or ambient (physiological) heating). The first step in the fabrication of the SMP basket is to mold the basket structure as a two-dimensional part. The mold is fabricated by chemically etching or machining the grooves that will form the structure into a flat plate. This mold plate 1303 is then clamped between two ridged plates to form the completed mold. There is a port in the center of one of the outside plates to allow the injection of the uncured thermosetting SMP. The filled mold is allowed to rest at room temperature temporarily and then heated to accelerate curing of the SMP. Injection molding a thermoplastic SMP is also feasible. A penny 1304 is shown positioned next to the mold plate 1303.

The fabrication process involves forming the two-dimensional (as molded) part 1300 into the three-dimensional primary "open basket" shape 1102 using a mandrel (male) and die (female) in the shape of the desired structure. The two-dimensional part 1300 is placed into the die and heated to soften the SMP. The mandrel is heated separately and then placed into the heated die, capturing the two-dimensional part between the die and the mandrel and forcing it into the "open basket" shape. The assembled mold is then heated above the highest glass transition temperature of the SMP and cooled to set the primary shape. The last step in the fabrication process is to form the SMP basket 1102 into the secondary tube shape 1200 that will act as an extension of the catheter prior to actuation. The part is placed on a mandrel that is heated slightly above the soft phase glass transition temperature of the SMP (to soften the SMP) and pulled through a series of heated tubes. This process is repeated as the size of the mandrel and tubes are reduced until the final, fully collapsed tube shape 1200 is formed.

Figure 14:
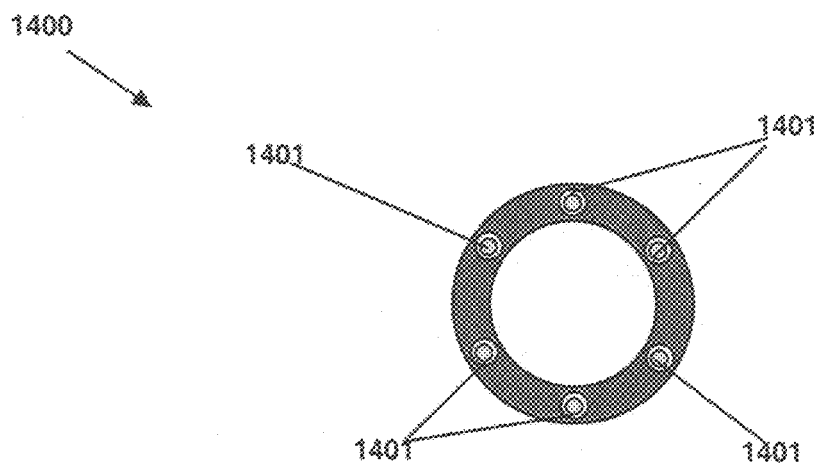
FIG. 14 is an illustration of an actuator for acting upon a material in a vessel of the present invention.

Referring now to FIG. 14, an illustration of a catheter for laser heating of an actuator for acting upon a material in a vessel of the present invention is shown. This embodiment is designated generally by the reference numeral 1400. The embodiment 1400 is an example of a multi-lumen catheter containing six optical fibers 1401 with a front-view being illustrated. Laser light emerging from the distal ends of the optical fibers 1401 propagates directly into the SMP basket (not shown) mounted to the distal end of the catheter 1400. The main central lumen allows delivery of the SMP coil device.

The structural components of the embodiment 1400 having been described and illustrated in FIG. 14, the construction and operation of the embodiment 1400 will now be described. The SMP basket is doped with laser-absorbing dye by soaking in a solvent with dissolved dye or by dipcoating in a solution consisting of dye and SMP dissolved in a solvent and then vacuum drying (uniform or graded dye concentration) or by dissolving the dye in the liquid SMP prior to curing. Using an index-matched epoxy at the interface, the SMP basket, in its secondary tube form, is mounted to a multi-lumen catheter containing several optical fibers 1401. The optical fibers 1401 are coupled to a laser source external to the body.

Figure 15:
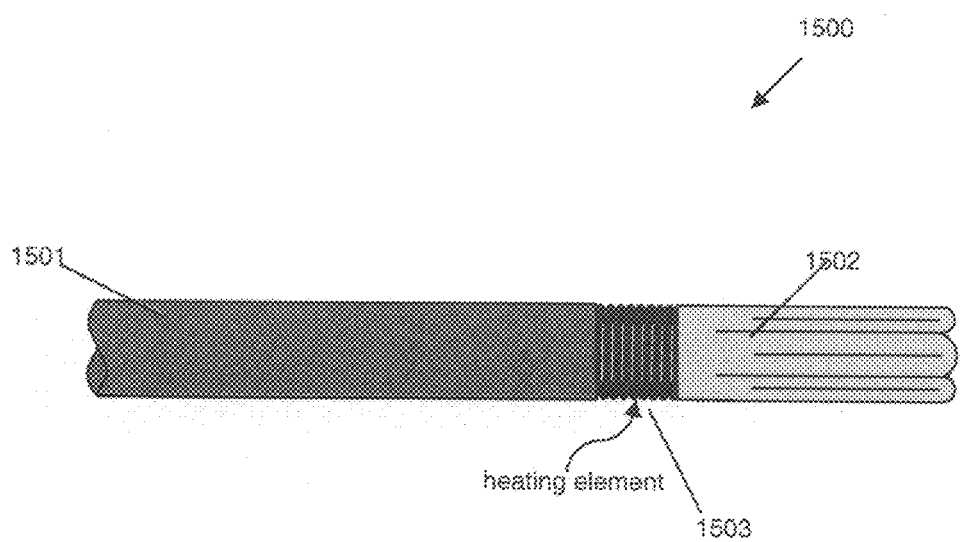
FIG. 15 is an illustration of another embodiment of a shape memory polymer basket system of the present invention.

Referring now to the drawings and in particular to FIG. 15, an illustration of another embodiment of a shape memory polymer basket system of the present invention is shown. The shape memory polymer basket system of this embodiment is designated generally by the reference numeral 1500. The shape memory polymer basket system 1500 includes the following structural components: catheter 1501, an expandable basket 1502, and a heating element 1503 between the catheter 1501 and the expandable basket 1502. The heating element 1503 is a hollow-core resistive heating element which is attached with leads (not shown) to a power supply external to the body. The shape memory polymer basket 1500 comprises a shape memory polymer (SMP), a polymer that can be formed into a primary or equilibrium shape, re-formed into a stable secondary or stressed shape, and actuated by controlled heating to recover its primary shape.

The structural components of the shape memory polymer basket 1500 having been described and illustrated in FIG. 15, the construction and operation of the shape memory polymer basket 1500 will now be described. The shape memory polymer basket 1500 provides a mechanical device to remove non-vascular or vascular occlusions (e.g., blood clot) from the body. The heating element 1503 is used for actuation of the expandable basket 1502. The shape memory polymer basket 1500 can be described as a hot catheter tip with attached SMP basket in tube form. The catheter 1501 tip is comprised of a resistive heating element 1503 (in this case a wire coil matching the catheter diameter) which serves as an extension of the catheter 1501. The SMP basket 1502 is mounted directly to the heating element 1503.

Alternatively, saline could be injected through the catheter 1501 which would be heated by the resistive element 1503 and in turn would heat the SMP basket 1502 as it passes out of the catheter 1501, causing it to expand into the "open basket" shape. In the SMP basket with a heated saline flush system 1500, the electrical heating element 1503 (or series of heating elements) is placed inside the distal end of the catheter 1501 to which the SMP basket is mounted. The element(s) 1503 is positioned to allow delivery of the SMP coil device through the catheter 1501. A saline bolus is slowly pushed through the catheter 1501 and heated by the heating element(s) 1503 as it exits the catheter 1501 and passes by the attached SMP basket in its tube form. The heated saline actuates the basket into its "open basket" form.

Figure 16:
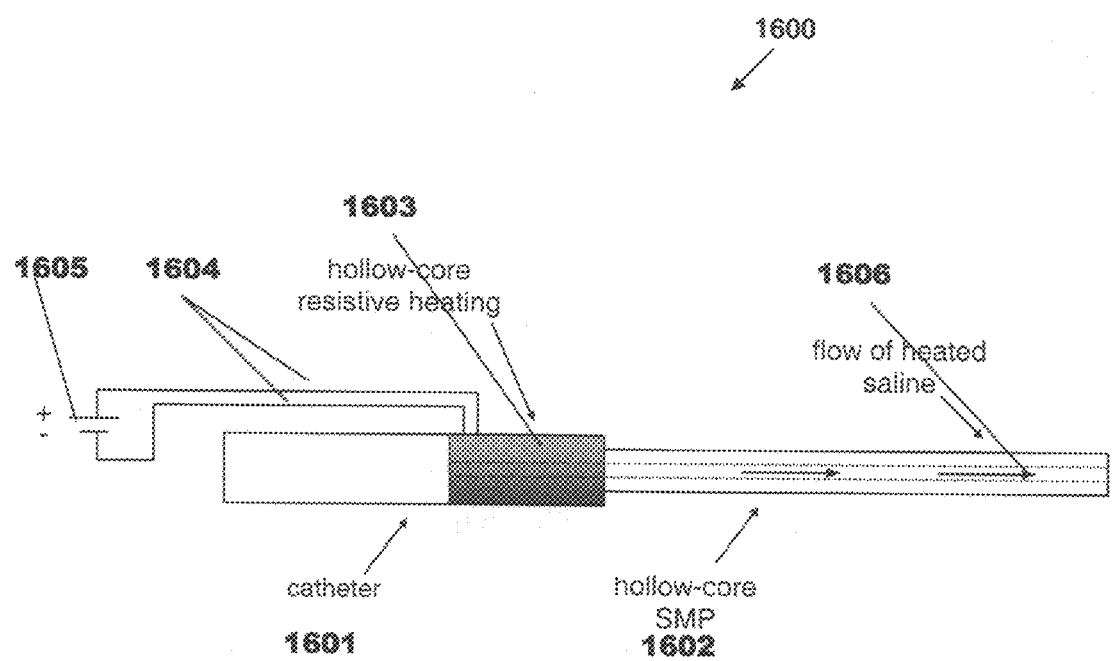
FIG. 16 is an illustration of another embodiment of a hollow-core SMP coil with a heated saline flush system of the present invention.

Referring now to the drawings and in particular to FIG. 16, an illustration of another embodiment of a hollow-core SMP coil with a heated saline flush system of the present invention is shown. The hollow-core SMP coil with a heated saline flush system of this embodiment is designated generally by the reference numeral 1600. The hollow-core SMP coil with a heated saline flush system 1600 includes the following structural components: catheter 1601 comprising the transport vehicle, a hollow-core SMP 1602, a hollow-core resistive heating element 1603, and a saline solution 1606. The hollow-core resistive heating element 1603 is attached with leads 1604 to a power supply 1605 external to the body. The hollow-core SMP 1602 comprises a shape memory polymer (SMP), a polymer that can be formed into a primary or equilibrium shape, re-formed into a stable secondary or stressed shape, and actuated by controlled heating to recover its primary shape.

The structural components of the hollow-core SMP coil with a heated saline flush system 1600 having been described and illustrated in FIG. 16, the construction and operation of the hollow-core SMP coil with a heated saline flush system 1600 will now be described. The core of the SMP coil 1602 is hollow, forming a small flow channel down the center of the coil. At the attachment point of the SMP coil 1602 to the catheter 1601 is a hollow-core resistive heating element 1603, which is attached with leads 1604 to a power supply 1605 external to the body. When the SMP coil 1602 is to be actuated, power is supplied to the heating element 1603 and a saline solution 1606 is pushed through the catheter 1601. The saline solution 1606 flows through the heating element 1603, increases in temperature, and then flows through the flow channel in the SMP coil 1602. The heated fluid 1606 actuates the coil 1602 into its primary "corkscrew" shape. In another embodiment, for enhanced heat transfer from the heated saline fluid 1606, a tortuous flow channel is designed into the core of the SMP coil 1602.

Figure 17:
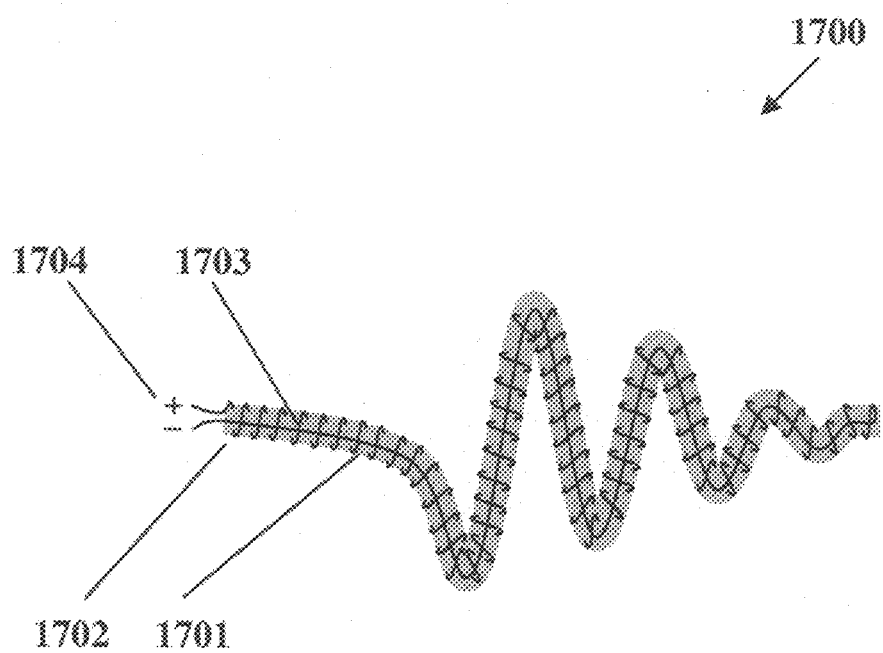
FIG. 17 is an illustration of a shape memory polymer coil of one embodiment of an actuator for acting upon a material in a vessel.

Referring now to the drawings and in particular to FIG. 17, an illustration of a shape memory polymer coil of one embodiment of an actuator for acting upon a material in a vessel of the present invention is shown. The shape memory polymer coil of this embodiment is designated generally by the reference numeral 1700. The shape memory polymer coil 1700 includes the following structural components: a coil corkscrew body 1701, a proximal end 1702, resistive heating element 1703, and a power source 1704. The shape memory polymer coil 1700 is attached to the distal end of a guide wire (not shown). The shape memory polymer coil 1700 comprises a shape memory polymer (SMP), a polymer that can be formed into a primary or equilibrium shape, re-formed into a stable secondary or stressed shape, and actuated by controlled heating to recover its primary shape.

The structural components of the shape memory polymer coil 1700 having been described and illustrated in FIG. 17, the construction and operation of the shape memory polymer coil 1700 will now be described. The shape memory polymer coil 1701 contains the resistive heating element 1703 (metal wire) designed to enhance recovery of the "corkscrew" shape. The wire 1703 extends distally through the SMP 1701 and is wrapped back around the SMP 1701 while in its "corkscrew" form. The part is then coated with SMP to insulate the outer wrapped wire 1703. The spring force of the wrapped wire 1703 will assist recovery of the coil shape. The terminals of the wire extend beyond the proximal end 1702 of the SMP and are connected to leads running through the guide wire that are connected to a power supply 1704.

Figure 18:
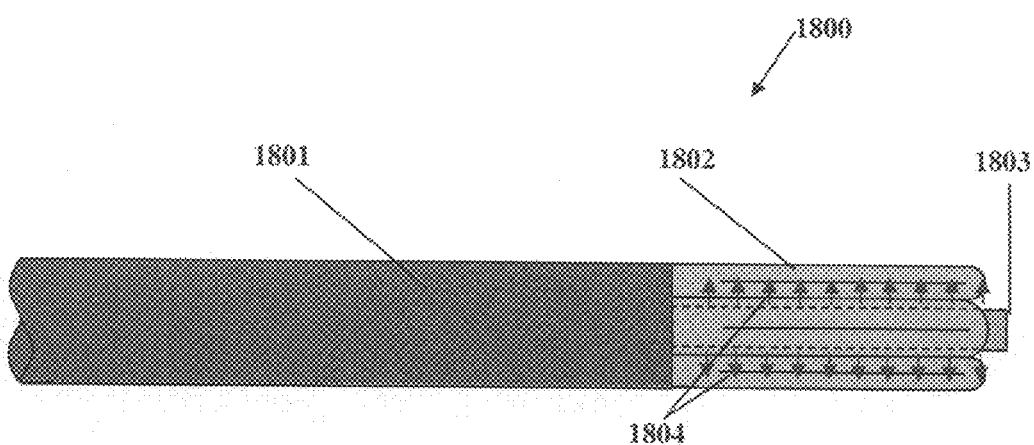
FIG. 18 is an illustration of another embodiment of a SMP basket with a removable diffusing optical fiber of an actuator for acting upon a material in a vessel.

Referring now to FIG. 18, an illustration of another embodiment of a SMP basket with a removable diffusing optical fiber for laser heating of an actuator for acting upon a material in a vessel of the present invention is shown. The SMP basket with a removable diffusing optical fiber of this embodiment is designated generally by the reference numeral 1800. The SMP basket with a removable diffusing optical fiber 1800 includes the following structural components: a catheter 1801, an expandable basket 1802, and a diffusing tip optical fiber 1803. The diffusing optical fiber 1803 is positioned inside the SMP basket 1802. Laser light represented by the arrows 1804 diffuses outward from the fiber 1803 and heats the SMP basket 1802 resulting in actuation of the basket 1802. The diffusing optical fiber 1803 is then withdrawn to restore the catheter lumen.

The structural components of the SMP basket with a removable diffusing optical fiber 1800 having been described and illustrated in FIG. 18, the construction and operation of the SMP basket with a removable diffusing optical fiber 1800 will now be described. The SMP basket 1802 is doped with laser-absorbing dye by dipcoating in solution containing dye (e.g., SMP and dye dissolved in solvent) or soaking in a solvent with dissolved dye (uniform or graded dye concentration), or by dissolving the dye in the liquid SMP prior to curing. The SMP basket 1802, in its secondary tube form, is mounted to the catheter 1801 using epoxy (or by other suitable means). A diffusing tip optical fiber 1803 which is coupled to a laser source external to the body is inserted through the catheter 1801 such that the diffusing portion of the fiber 1803 is situated inside the basket 1802. Light 1804 diffusing outward from the fiber 1803 is absorbed by the basket 1802, resulting in thermal actuation. After actuation, the diffusing fiber 1803 is withdrawn. The SMP expandable basket 1800 may be coupled with any of the SMP coil designs described herein to complete the occlusion removal device. The SMP basket is designed in a way that allows it to be heated and reformed or consolidated from its primary "open basket" shape into a secondary tubular shape shown in FIG. 18 that initially acts as a distal extension of the catheter. Upon heating above its transition temperature, the SMP basket expands to recover its primary "open basket" form. The device is shown in its pre-actuation collapsed form in FIG. 18.

Referring now to the drawings and in particular to FIG. 19A, FIG. 19B, FIG. 19C, and FIG. 19D a series of four diagrams are shown illustrating principles of operation of the shape memory polymer expandable coil 1902 and the shape memory polymer basket 1901. The shape memory polymer expandable coil 1902 is attached to a guide wire 1905 and the shape memory polymer basket 1901 is situated at the distal end of a catheter 1903. The catheter 1903 is moved through a guide catheter 1904.

Figure 19:
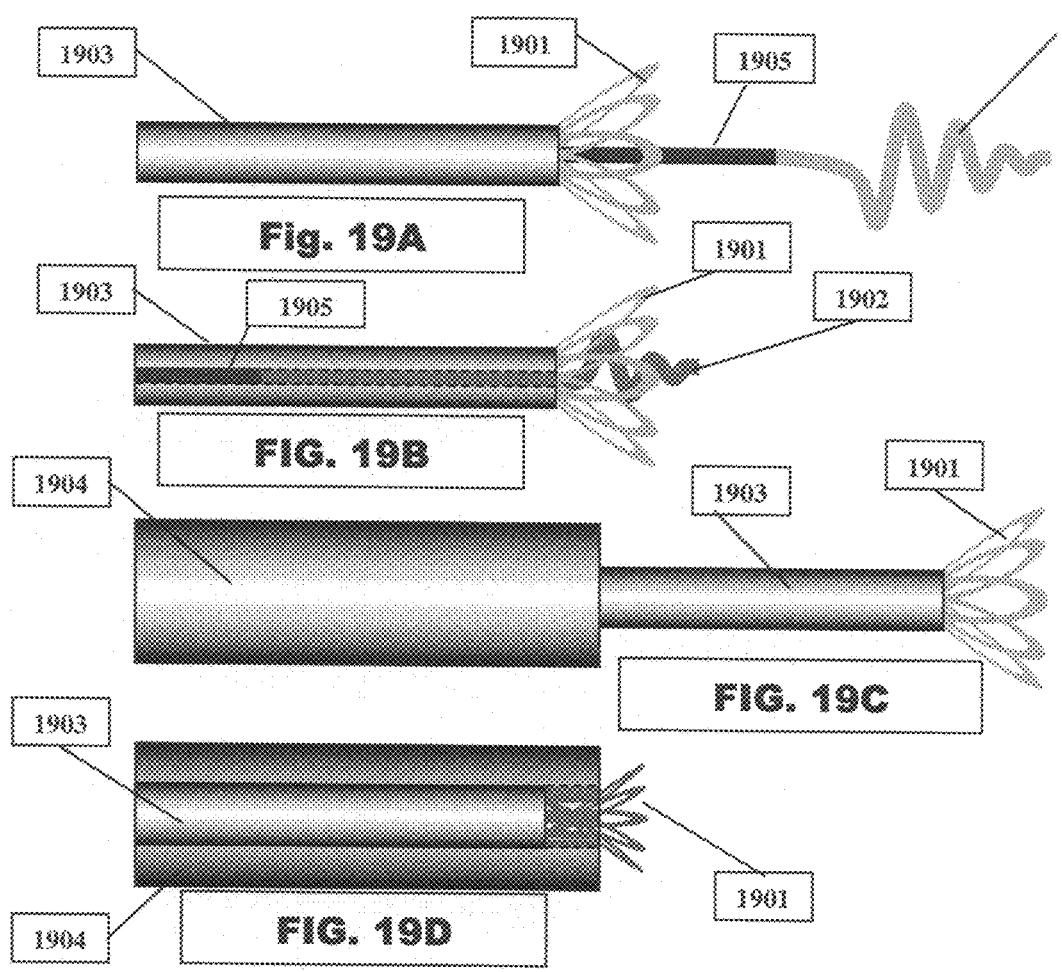
FIGS. 19A, 19B, 19C, and 19D are a series of four diagrams illustrating principles of operation of the shape memory polymer expandable coil and the shape memory polymer basket.

The structural components of the shape memory polymer basket 1901 and the shape memory polymer expandable coil 1902 having been described and illustrated in FIG. 19, the construction and operation of the system will now be described. The system uses bi-directional operation of the SMP coil and basket devices using a sheathing technique. In FIG. 19A the SMP coil 1902 and the basket 1901 are shown in their expanded forms. The FIG. 19B shows the SMP coil 1902 having been heated (causing it to soften) and simultaneously retracted into the catheter 1903 which forces the coil 1902 to straighten. In FIG. 19C, the SMP basket 1901 is shown in its expanded "open" form extending from the guide catheter 1904. In FIG. 19D, the SMP basket 1901 has been heated and retracted into the guide catheter 1904, forcing the basket 1901 to assume its "closed" form.

Alone, the SMP coil 1902 and basket 1901 are capable of one-way actuation; that is, upon heating, they change from the stable secondary shape to the primary shape. The coil 1902 will change from a straight rod shape into the "corkscrew" shape and the basket 1901 will change from the "closed" tube form to the "open" basket form. However, both of these devices can be reset into their original secondary shapes and re-deployed if necessary, without the need to withdraw the devices from the body. This is accomplished by using the catheter 1903 and guide catheter 1904 as a sheath to constrain the SMP coil and basket devices, respectively, while they are being heated (independent of the type of heating mechanism). For example, the coil device may be re-heated after previous actuation and retracted back into the catheter. Because the SMP softens when heated, it will straighten as it is pulled back into the catheter. Once it is fully constrained, the heating source is turned off, causing the device to resume its straight form. Likewise, the "open" SMP basket may be retracted back into the guide catheter while it is heated, causing it to resume its "closed" tube form. Conceivably, separate "sheathing devices" could be incorporated rather than using the catheters themselves to act as the sheaths.

Referring now to the drawings and in particular to FIG. 20A and FIG. 20B, two diagrams are shown to illustrate principles of operation of the shape memory polymer expandable coil 2000. In FIG. 20A the shape memory polymer expandable coil 2000 is shown in its collapsed secondary form wherein the coil 2000 can be pushed distally through an occlusion. In FIG. 20B the shape memory polymer expandable coil 2000 is shown in its expanded primary form wherein the expanded coil 2000 can capture the occlusion.

In order to increase the shape recovery force of an SMP actuator/device, a material 2001 (e.g., metal wire, elastic or superelastic metal wire, shape memory alloy, or other non-metal material) configured such that when deformed it tends to resume its original shape is incorporated into the SMP device. The recovery enhancing material can be inside (e.g., embedded in) or outside (e.g., attached to or encasing) the SMP portion of the device 2002. The preferred shape of this recovery enhancing material corresponds to the desired recovered shape of the SMP device.

Figure 20:
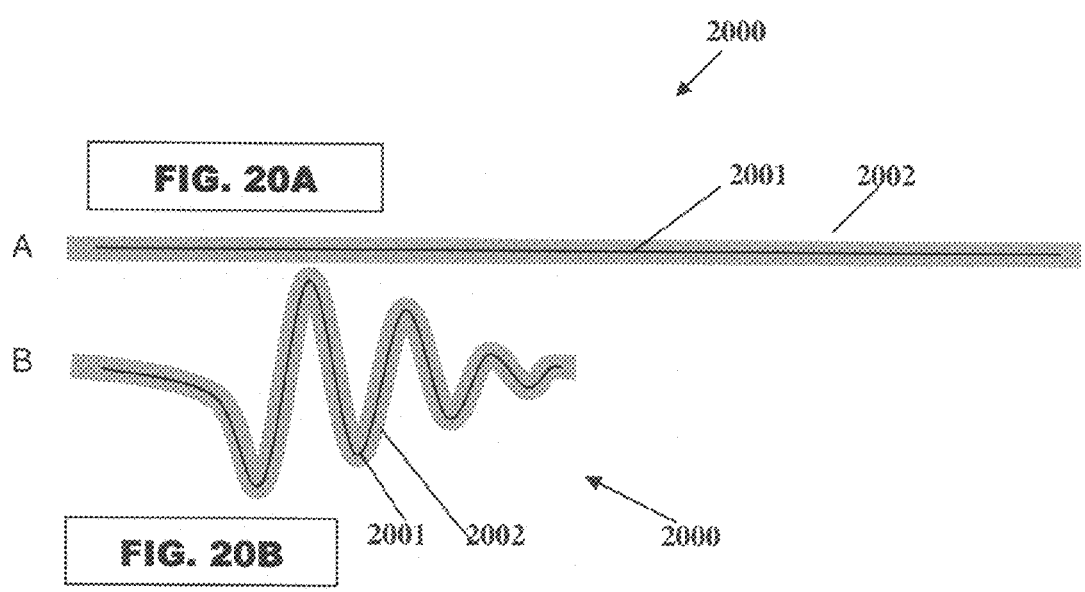
FIGS. 20A and 20B are two diagrams that illustrate principles of operation of the shape memory polymer expandable coil.

As illustrated in FIG. 20 A and FIG. 20B, a superelastic wire "spring" 2001 in the shape of a coil is embedded in the SMP material 2002. The "spring" 2001 could be dip-coated in thermoplastic SMP 2002 or it could be incorporated into thermosetting SMP 2002 during injection molding. The primary (recovery) shape of the SMP 2002 corresponds to the preferred shape of the inner "spring 2001." When heated above the SMP transition temperature, the device is deformed into a stable secondary shape (e.g., straight rod) and then cooled. The inner "spring" is constrained by the SMP in its stable secondary shape. Upon heating again above the SMP transition temperature, the modulus of the SMP decreases (softens) as it resumes its primary coil shape, simultaneously allowing the inner "spring" to resume its preferred coil shape. The "spring" could serve as a resistive element in the case of actuation by resistive heating, in which case a return path (using the same wire or by attaching another type of conductive wire) is necessary to complete the current loop. Otherwise, other means of thermal actuation such as laser heating or inductive heating could be used. It is possible that the inner "spring" could be made to absorb laser light for laser heating or be made of a ferromagnetic material for inductive heating.

In another possible embodiment, the superelastic "spring" could be hollow (e.g., tube or wire windings) and the SMP could be inside the "spring."

Figure 21:
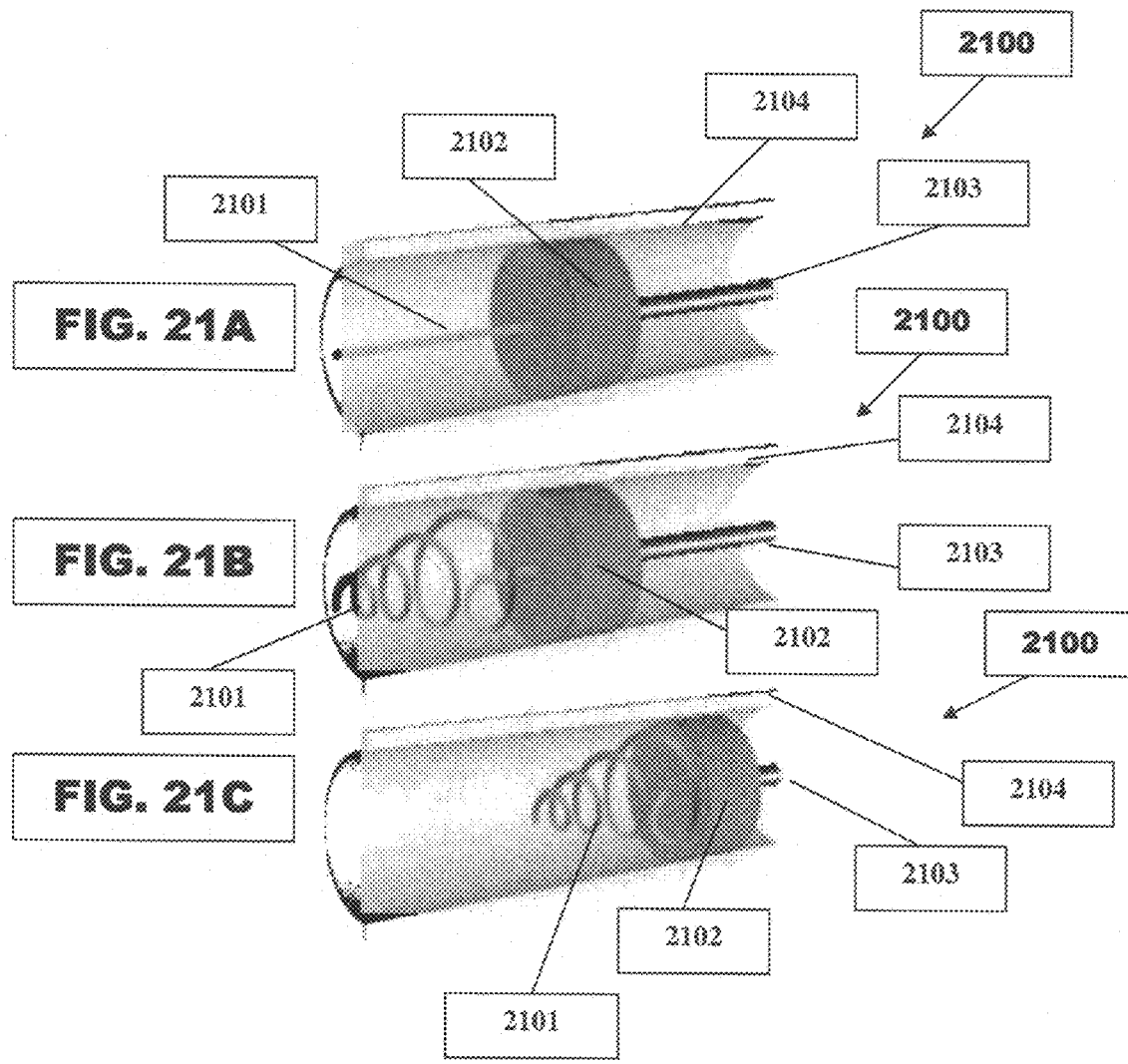
FIGS. 21A, 21B, and 21C are a series of three diagrams illustrating principles of operation of the shape memory polymer expandable coil system.

Referring again to the drawings and in particular to FIG. 21A, FIG. 21B, and FIG. 21C, a series of three diagrams is shown illustrating principles of operation of the shape memory polymer expandable coil 2100 system. The three diagrams, FIG. 21A, FIG. 21B, and FIG. 21C, are a depiction of endovascular thrombus removal using a SMP microactuator 2100 consisting of a SMP expandable coil 2101 mounted to a guide wire 2103. In its secondary straight rod form 2101 shown in FIG. 21A, the microactuator 2100 is delivered through a catheter (not shown) distal to the vascular occlusion 2102 in a blood vessel 2104. The distal end of the microactuator 2100 penetrates the occlusion 2102. The rod 2101 is transformed into its primary corkscrew shape by laser heating as shown in FIG. 21B. The microactuator 2100 is retracted with the rod 2101 in its expanded corkscrew shape and the captured thrombus 2102 is removed to restore blood flow. The SMP basket is not shown.

Due to the narrow (3-hour) treatment window for effective use of the thrombolytic drug recombinant tissue-type plasminogen activator (rt-PA), there is a need to develop alternative treatments for ischemic stroke. The shape memory polymer expandable coil 2100 system provides an intravascular device for mechanical thrombus removal using shape memory polymer (SMP). The shape memory polymer expandable coil 2100 system makes it possible to deliver the SMP microactuator 2101 in its secondary straight rod form (length=4 cm, diameter=350 µm) illustrated in FIG. 21A through a catheter distal to the vascular occlusion 2102. The microactuator 2101, which is mounted on the end of an optical fiber, is then transformed into its primary corkscrew shape by laser heating (diode laser, $\lambda$=800 nm) above its soft phase glass transition temperature (Tgs=55° C.). Once deployed, the microactuator 2100 is retracted and the captured thrombus 2102 is removed to restore blood flow. The SMP 2101 is doped with indocyanine green (ICG) dye to increase absorption of the laser light. Successful deployment of the microactuator 2100 depends on the optical properties of the ICG-doped SMP and the optical coupling efficiency of the interface between the optical fiber and the SMP. Spectrophotometry, thermal imaging, and computer simulation aided the initial design effort and continue to be useful tools for optimization of the dye concentration and laser power.

The only approved treatment for acute ischemic stroke is intravenous administration of recombinant tissue-type plasminogen activator (rt-PA). This thrombolytic drug, which is infused over a 1 hour period, restores blood flow by chemically dissolving the thrombus following ischemic stroke. A Phase III multicenter clinical trial demonstrated beneficial outcomes when rt-PA was administered within 3 hours of the onset of stroke symptoms, though patients treated within 90 minutes showed the most benefit. In a separate Phase III trial, patients treated 3-5 hours after symptom onset showed no benefit, confirming that rt-PA should only be administered within 3 hours. However, the majority of patients are not eligible to receive intravenous rt-PA, mainly due to delays in obtaining treatment. Additional drawbacks of rt-PA include the relatively high risk of intracranial hemorrhage, the numerous contraindications prohibiting treatment, and the extensive patient follow-up monitoring and care associated with systemic thrombolytic drug exposure. A potential alternative to rt-PA is mechanical removal of the thrombus using the microdevice 2100 deployed endovascularly. The microdevice

2100 provides a catheter-based SMP device to capture and remove the thrombus 2102 and restore blood flow following ischemic stroke.

The microdevice 2100 was fabricated using a commercially available thermoplastic SMP (MM5520, DIAPLEX Company, Ltd., a subsidiary of Mitsubishi Heavy Industries, Ltd., Tokyo, Japan). Recovery of the stable primary shape is achieved by controlled heating of the SMP in its stable secondary shape. While heated above its highest glass transition temperature (Tg≈130° C.), the SMP is formed into the primary shape and cooled to stabilize the shape. At a temperature above its soft phase glass transition temperature (Tgs=55° C.), the SMP is deformed into a secondary shape and then cooled. The primary shape is recovered by heating again to Tgs.

The present invention provides an endovascular thrombus removal system using a SMP micoroactuator. The endovascular thrombus removal system comprises a transport vehicle, a shape memory material operatively connected to said transport vehicle, said shape memory material adapted to move from a first shape that can be moved through said vessel, to a second and different shape for acting upon said thrombus, and a heat transfer mechanism operatively connected to said shape memory material, adapted to transfer heat to said shape memory material to move said shape memory material from said first shape to said second shape. The figures of drawings 1-21, and in particular FIGS. 3A-C and FIGS. 21A-C, provide embodiments illustrating principles of operation of the endovascular thrombus removal system. For example, as illustrated in FIGS. 21A-C, the microactuator 2100 is delivered through a catheter distal to the vascular occlusion 2102. The distal end of the microactuator 2100 penetrates the occlusion 2102. The rod 2101 is transformed into its primary corkscrew shape by laser heating as shown in FIG. 21B. The microactuator 2100 is retracted with the rod 2101 in its expanded corkscrew shape and the captured thrombus 2102 is removed to restore blood flow.

Individual embodiments of the microactuator were constructed and tested. In the microactuator fabrication, raw SMP material was extruded into a strand with circular cross-section approximately 350 μm in diameter. A cylindrical rod segment approximately 4 cm in length was obtained. In one end of the segment, a hole (diameter=127 μm, depth=1 mm) was drilled coaxial with the longitudinal axis of the rod. A multimode ultra low-OH 100 μm core diameter (125 μm diameter including the polyimide buffer) step-index silica core/silica clad optical fiber (FIP100110125, Polymicro Technologies, Phoenix, Ariz.) was cleaved on one end (numerical aperture=0.22). The other end (terminated with an ST connector) was coupled to a pigtailed 800 nm diode laser (H01-A001-800-FC/100, Opto Power Corporation, Tucson, Ariz.). The cleaved end of the fiber was inserted into the drilled socket in the SMP rod and secured with a fast-setting epoxy (Double-Bubble Red #04001, Hardman, Inc., Belleville, N.J.) around the joint. The tip of the drill bit used to create the socket was slightly convex, resulting in a small air gap between the cleaved fiber tip and the SMP.

An illustration of the fiber-SMP joint is illustrated in FIG. 4. The cleaved end of the optical fiber is inserted into the drilled socket in the SMP rod. The glass core of the fiber is slightly exposed at the cleaved end where the polyimide buffer was removed prior to cleaving. The resulting air gap where the socket end meets the cleaved fiber tip is apparent (index-matched epoxy was not used in the socket in this case). Epoxy applied external to the socket secures the joint. The cleaved end of the optical fiber is inserted into a coaxial socket in the SMP rod and bonded in place with epoxy. Because the drill bit used to create the socket yielded a slight convex surface at the end of the socket, a small air gap exists between the cleaved fiber tip and the SMP. Some epoxy typically migrates slightly into the socket before curing (not shown).

After the epoxy was fully cured, the SMP rod was wrapped around a cone-shaped aluminum mandrel illustrated in FIG. 5 to set the primary corkscrew shape. A narrow channel machined around the mandrel and an aluminum cap placed over the mandrel captured the wrapped SMP rod and maintained the corkscrew form during the heating procedure. The mandrel assembly was placed in a hot air stream (Model 185-A, Beahm Designs, Los Gatos, Calif.) at approximately 130° C. for 15-20 minutes and then cooled to room temperature to set the primary shape. The SMP microactuator is illustrated in its corkscrew form in FIG. 1. The corkscrew shape was chosen to maintain the waveguiding ability of the SMP microactuator while providing a means of capturing a thrombus. After removing the SMP from the mandrel, it was placed in the hot air stream at approximately 75° C. and manually straightened into its secondary rod shape, and then cooled to set the secondary shape prior to laser actuation.

The circular cross-section of the SMP microactuator enhances its waveguiding ability, enabling light to propagate along its entire length with minimal loss due to leakage. In order to increase absorption of the 800 nm diode laser light and enhance heating, the SMP rods were doped with indocyanine green (ICG) dye (Sigma Chemical Co., St. Louis, Mo.) which has a strong absorption peak near 800 nm. Prior to drilling the hole in the SMP rod, the rod was soaked in a solution of ICG dye and methanol, allowing the ICG dye to diffuse into the SMP, and then vacuum dried to remove the methanol. The concentration of ICG in the SMP rod was estimated based on the ICG concentration in the methanol and amount of methanol that diffused into the SMP; the ICG concentration in the SMP was assumed to be uniform. Rods with ICG concentrations from approximately 0.08 to 4.7 μM were made.

The absorption coefficient of the ICG-doped SMP was calculated for various ICG concentrations. Using a spectrophotometer (Cary 300, Varian Instruments, Walnut Creek, Calif.), the spectral absorbance of thin samples of thermoset SMP (MP5510, DIAPLEX Company, Ltd.) with various ICG dye concentrations (0-40.6 μM) was measured. The thermoset material, which is easily molded into thin films unlike the thermoplastic material used for the device, was used to facilitate fabrication of the samples. Also, because it is in a liquid state prior to curing, the ICG dye was added directly to the uncured material, allowing uniform distribution of the dye and accurate control of the concentration. After removing the contribution from reflective losses inherent in the measurement, the absorbance data were used to calculate the absorption coefficient, μa, at the laser wavelength (800 nm) as a function of ICG dye concentration:

$$\mu_a = \frac{A}{d} \ln 10 \qquad (1)$$

where A is the absorbance, d is the sample thickness, and ln is the natural logarithm (ln 10=2.303). The absorption coefficient varies linearly with absorbance.

In order to estimate the absorption of ICG-doped thermoplastic, the absorbance of a thin sample of thermoplastic SMP without dye was measured. Because the absorbance value at 800 nm was within the noise level of the measurement (i.e., reflective losses exceeded actual absorption), it was estimated to be zero. In contrast, the thermoset material without dye had measurable (nonzero) absorbance at 800 nm. Assuming the dependence of absorbance on dye concentration is the same for thermoplastic and thermoset SMP, the thermoset absorption coefficient versus dye concentration curve was simply shifted down to intercept the origin to estimate the thermoplastic absorption.

Because the photon mean free path (i.e., the average distance a photon will travel before being absorbed, ignoring scattering) is simply the reciprocal of the absorption coefficient, the absorption coefficient provides information regarding the penetration depth of the light in ICG-doped SMP. Ignoring loss mechanisms other than absorption, the amount of light decreases exponentially with distance into the SMP:

$$T = \exp(-\mu_a d) \quad (2)$$

where T is the fraction of light transmitted and d is the distance traveled. At a distance equal to the photon mean free path (d=1/µa), the amount of light drops to 37% (T=0.37).

An infrared camera (Thermacam PM250, Inframetrics, Billerica, Mass.) with a close-up lens was used to measure the temperature of the SMP rod upon laser heating. For these experiments, the corkscrew shape was not set and the rod was left in its straight form to eliminate movement during heating and facilitate temperature measurement along its length. Temperature distributions were observed for various ICG dye concentrations and laser powers.

Because laser light is used to actuate the device, its success depends on the ability of the SMP to behave as a waveguide. In its straight form, the cylindrical SMP rod suffers no leakage, much like an optical fiber. However, because laser heating must continue as the SMP changes shape, ZEMAX optical design software (ZEMAX Development Corporation, San Diego, Calif.) was used to model the light transmission from the optical fiber through the SMP microactuator in its corkscrew form. Light loss due to leakage out of the SMP was estimated for device actuation in air and in blood. Because the actuation occurs as the SMP transforms, modeling the light propagation in its corkscrew form represents a worst-case scenario (i.e., the microactuator is initially straight when laser actuation begins).

In order to assess the feasibility of using the 100 µm core optical fiber in the tortuous paths encountered in the neurovasculature, the transmission of 800 nm laser light through a single 360° loop of the optical fiber was measured for various loop radii down to 1 mm. The amount of light exiting the looped fiber relative to the amount of light exiting the straight (no loop) fiber was measured using a power meter (LabMaster-E, Coherent, Inc., Santa Clara, Calif.) with a thermal sensor (LM-10, Coherent, Inc.).

Figure 22:
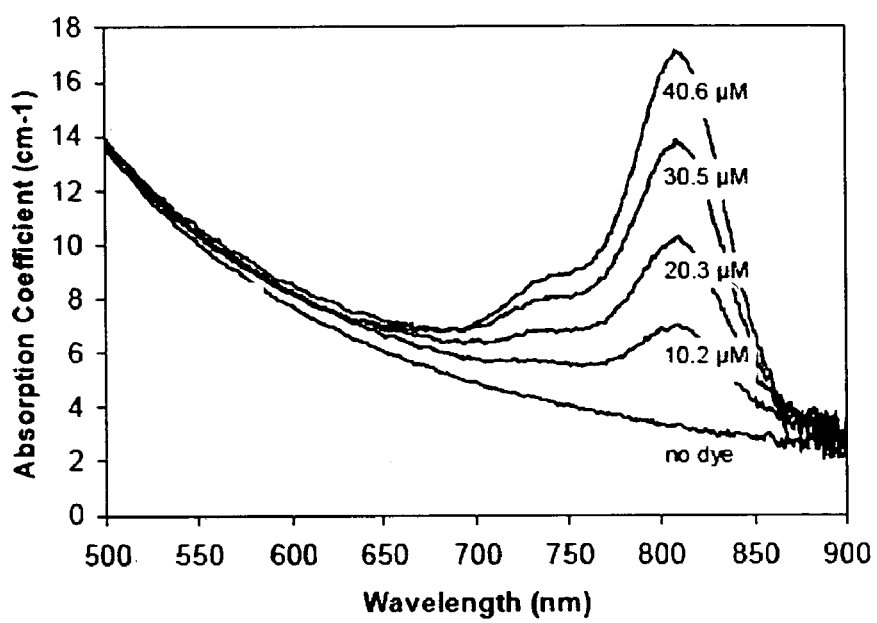
FIG. 22 illustrates the spectral absorption of shape memory polymer doped with laser-absorbing dye.

The spectral absorption of the thermoset SMP doped with ICG dye at concentrations from 0 to 40.6 µM is shown in FIG. 22. The estimated absorption coefficient at 800 nm for the thermoplastic SMP is plotted as a function of dye concentration in FIG. 23. As expected from the Beer-Lambert Law, the absorption coefficient varies linearly with ICG concentration at the relatively low concentrations tested. The photon mean free path (1/µa, ignoring scattering) is approximately equal to the length of the SMP rod (4 cm) at an ICG dye concentration of 0.8 µM. At this concentration, the amount of light reaching the distal end of the SMP rod has dropped to 37% (ignoring loss mechanisms other than absorption) according to equation (2). In comparison, the amount of light reaching the distal end of the SMP rod for a dye concentration of 0.08 µM is 91%.

Referring now to FIG. 22, the spectral absorption of thermoset SMP doped with ICG dye is illustrated. Dye concentrations of 10.2, 20.3, 30.5, and 40.6 µM were tested. Thermoset SMP with no dye was also tested.

Figure 23:
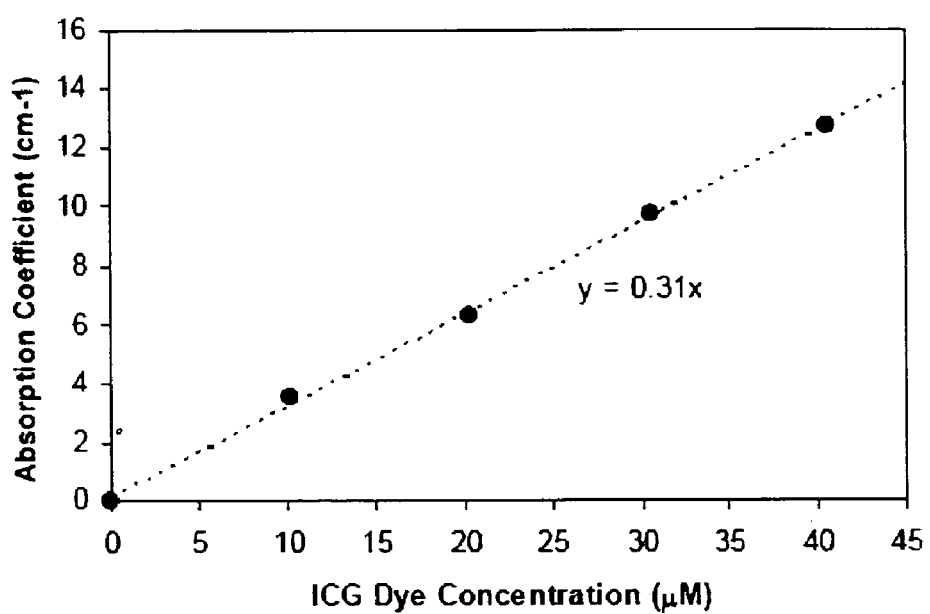
FIG. 23 illustrates the absorption coefficient of dye-doped shape memory polymer as a function of dye concentration.

Referring now to FIG. 23, an estimated absorption coefficient at 800 nm for thermoplastic SMP versus ICG dye concentration (data points) is illustrated. Dye concentrations of 0 (no dye), 10.2, 20.3, 30.5, and 40.6 µM were tested. A linear relationship exists between the absorption coefficient and dye concentration.

Observation of the straight SMP rod during laser heating with the thermal camera showed that the axial heat distribution depended on the ICG dye concentration. Lower dye concentrations resulted in more uniform axial laser heating along the straight SMP rod. However, the temperature at the fiber-SMP joint was sometimes independent of the dye concentration, reaching unexpectedly high temperatures even at the lowest dye concentration. In some cases, the elevated temperature at the joint approached or exceeded Tg, causing irreversible deformation and/or thermal damage of the SMP, which resulted in light leakage. It is likely that laser light back-reflected from the air-SMP boundary at the end of the drilled socket (Fresnel reflection due to index mismatch) was absorbed by the epoxy, causing the temperature in the vicinity of the joint to rise excessively. To test this hypothesis, several joints were created using an index-matched optically transparent epoxy (EPO-TEK 301-2, Epoxy Technology, Inc., Billerica, Mass.) applied in the socket, eliminating the air gap between the cleaved tip of the optical fiber and the SMP. Excessive heating at the joint was not evident in these samples, suggesting that the combination of the air gap and highly absorbing epoxy was responsible for the elevated temperature at the joint.

Figure 24:
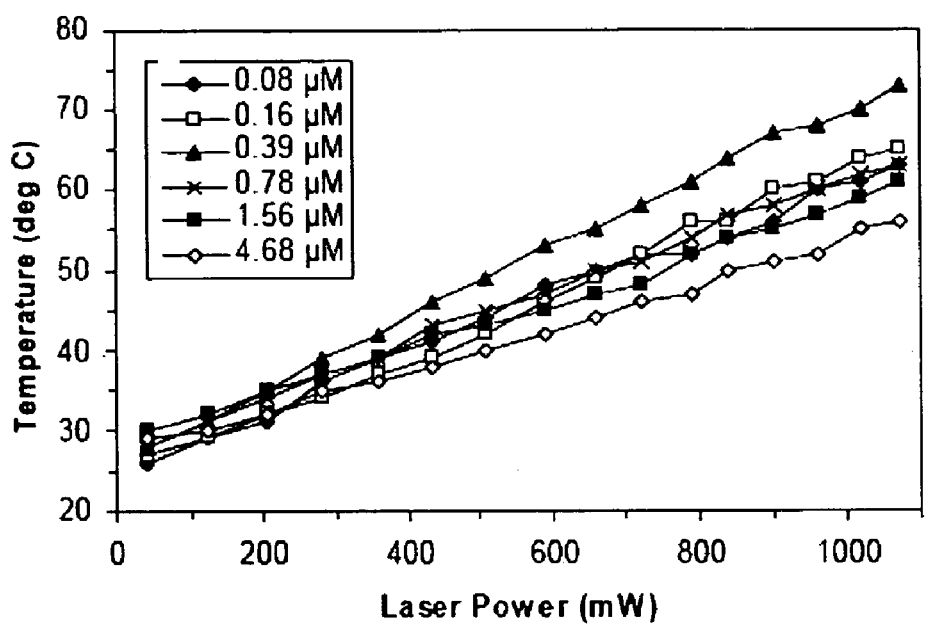
FIG. 24 illustrates the dependence of temperature of dye-doped shape memory polymer on laser power.

To elicit the dependence of temperature on ICG dye concentration and laser power, the temperature was measured at a point approximately 1 cm from the proximal (joint) end of the straight SMP rod for various dye concentrations as the laser power was slowly ramped up as shown in FIG. 24. The temperature increased linearly with laser power for all dye concentrations. The linear relationship was expected since the photon energy absorbed per unit volume (and, hence, the temperature rise), Eabs, at a given distance, d, along the SMP rod is proportional to the product of the absorption coefficient and the power per unit area (fluence) at the given distance:

$$E_{abs} \propto \mu_a \frac{\alpha P_0}{A_{cs}} \exp(-\mu_a d) \quad (3)$$

where P0 is the laser power output from the optical fiber, a is the fraction of light transmitted into the SMP ($\alpha$<1 due to Fresnel reflection and light leakage at the air gap in the socket), and Acs is the cross-sectional area of the SMP rod; the exponential accounts for the attenuation of the fluence due to absorption given by equation (2). Due to the inconsistent coupling of the laser light into the SMP (i.e., the value of $\alpha$ potentially varied from one experiment to the next), the slopes of the curves in FIG. 24 cannot be used to determine the relative efficiency of laser heating at the various dye concentrations.

Referring now to FIG. 24, the temperature 10 mm from the proximal (joint) end of the straight SMP rod versus laser power for ICG dye concentrations from 0.08 to 4.68 µM (data points) is illustrated. The temperature increased with laser power in a linear fashion for all dye concentrations.

Figure 25:
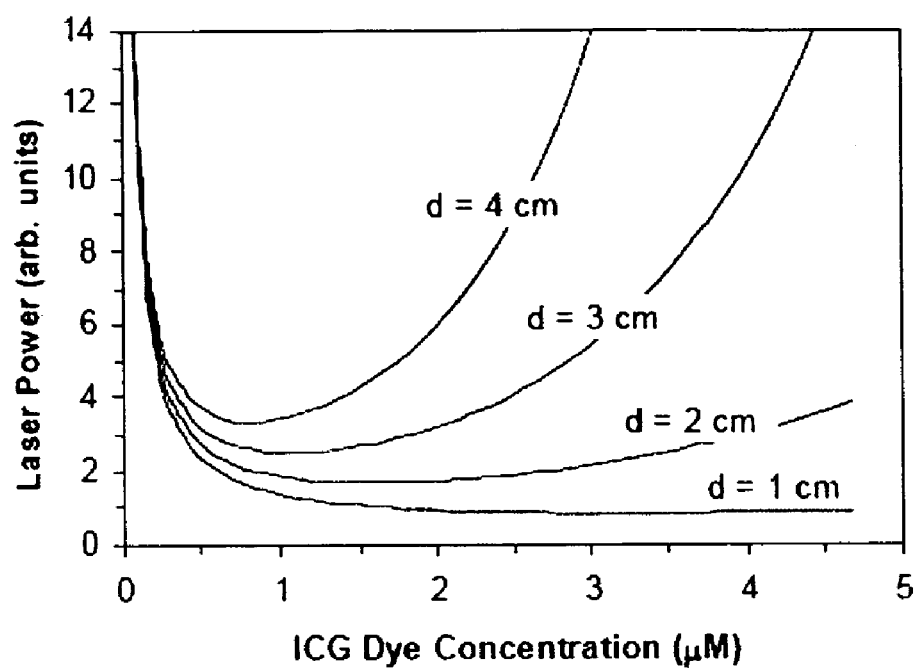
FIG. 25 illustrates the amount of laser power required to achieve a given temperature increase in dye-doped shape memory polymer.

The optimal dye concentration which minimizes the amount of laser power required to heat the SMP to a given temperature can be derived theoretically. Rearranging equation (3), noting that the temperature increase is directly proportional to the absorbed photon energy, and using the linear relationship between the absorption coefficient and the dye concentration shown in FIG. 23, the theoretical laser power needed to achieve a given temperature increase at a given distance along the SMP rod is plotted as a function of ICG dye concentration for various distances (FIG. 25). Isolating P0 in equation (3) and setting dP0/dµa (derivative of P0 with respect to µa) equal to zero yields a minimum of P0 at µa=1/d. Again using the linear relationship between the dye concentration and the absorption coefficient given in FIG. 23, P0 is minimized when the dye concentration is equal to 1/(0.31d). Note that this dye concentration is independent of the desired temperature increase; that is, this dye concentration will require the least amount of laser power to achieve any given temperature (e.g., Tgs) at a distance, d, along the SMP rod. For the 4 cm long SMP rod, the most efficient use of laser power occurs at a dye concentration of 0.8 µM (minimum laser power required to achieve a given temperature rise at d=4 cm).

Referring now to FIG. 25, the theoretical laser power required to achieve a given temperature increase versus ICG dye concentration at a distance of 1, 2, 3, or 4 cm from the proximal (joint) end of the straight SMP rod is illustrated. For the 4 cm long SMP rod, the most efficient use of laser power occurs at a dye concentration of 0.8 µM (minimum laser power required to achieve a given temperature rise at d=4 cm).

Figure 26:
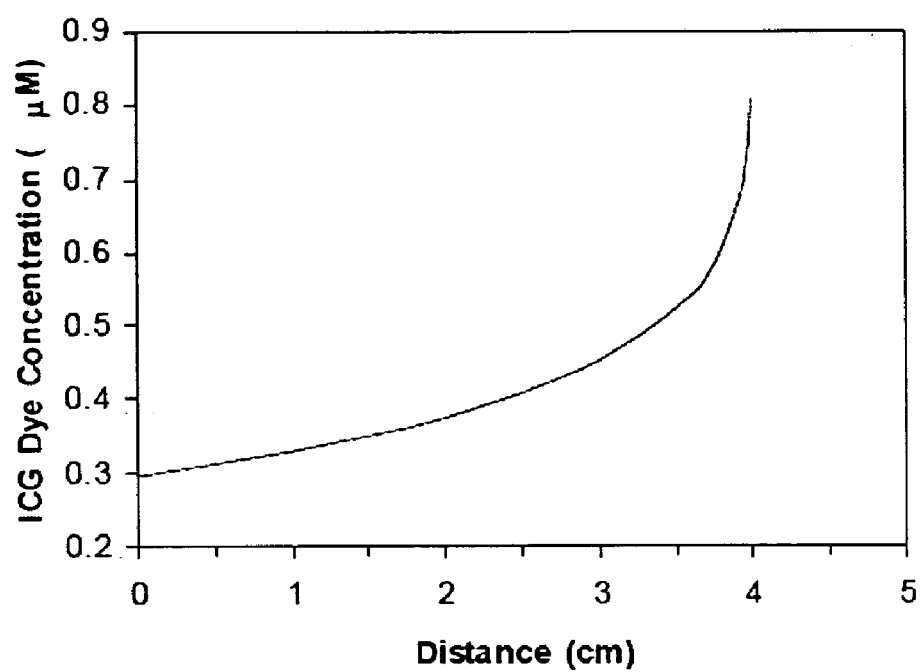
FIG. 26 illustrates a graded dye concentration profile.

Because more laser power is needed to achieve actuation of the SMP distally (farther from the fiber-SMP joint) versus proximally, a laser power must be chosen to achieve sufficient heating distally. As a result, proximal temperatures are higher than necessary. A non-uniform dye concentration in which the concentration gradually increased with distance from the joint would require less laser power and result in a more uniform axial temperature distribution. The optimal axial concentration profile is determined by rearranging equation (3) and using the linear relationship in FIG. 23 to obtain P0 as a function of the dye concentration, C:

$$P_0^{min} \propto \frac{1}{C} \exp(0.31Cd) = 3.37 \quad (4)$$

where Pmin0=3.37 is the minimum value of P 0 at d=4 cm, obtained by evaluating the expression in equation (4) at C=1/(0.31d), where d=4. FIG. 26 shows the dye concentration versus distance along the SMP rod obtained by numerically solving equation (4). This axial concentration profile would theoretically result in uniform axial heating of the SMP rod using the least amount of laser power.

Referring now to FIG. 26, the theoretical axial ICG dye concentration profile yielding uniform heating of the SMP rod using the least amount of laser power is illustrated. As more laser energy is absorbed as the light propagates through the SMP rod, more dye is required to maintain a constant temperature.

Successful laser actuation of the SMP device (i.e., complete recovery of the primary corkscrew shape) was achieved in air at ICG dye concentrations from 0.08 to 1.56 µM using laser powers from approximately 900 to 1100 mW. Higher and lower dye concentrations were not tested. Due to the excessive heating at the fiber-SMP joint, intermittent failures (partial or no actuation due to thermal deformation or damage of the SMP) also occurred at these dye concentrations.

A three-dimensional ray trace diagram illustrating light propagation through the SMP corkscrew was made. An air gap of 0.01 mm in the drilled socket between the cleaved tip of the optical fiber and the SMP was modeled, but the convex nature of the socket was not (it was assumed to be flat). Most of the 20 randomly selected light rays emitted by the optical fiber (numerical aperture=0.22) exit the SMP at the distal end, though some leak out early. Virtual detectors were placed along the SMP to monitor the amount of light at each location on the corkscrew. FIG. 27 provides a comparison of the amount of light loss versus distance along the corkscrew in air (index of refraction=1.00) and blood (index of refraction=1.38) with and without an air gap in the drilled socket. The higher index of refraction of blood results in increased light leakage. However, filling the air gap with a transparent material whose index of refraction matches that of the SMP (estimated to be 1.56 at 800 nm) reduces the amount of loss. The simulations suggest that elimination of the air gap will compensate for the negative effect of blood on the waveguiding ability of the SMP corkscrew.

A ZEMAX three-dimensional ray trace diagram of laser light propagation through the SMP microactuator in its corkscrew shape was made. The optical fiber entered the SMP at the end of the corkscrew. This ray trace was generated for a 0.01 mm air gap in the drilled socket between the cleaved tip of the optical fiber and the SMP, assuming the SMP device is in air. Virtual detectors placed along the corkscrew monitored the amount of light at each location to determine the effect of filling the air gap with a material with the same index of refraction as the SMP. As shown in FIG. 27 the percentage of light loss is plotted against distance along the corkscrew (data points). Additional simulations were performed to assess the waveguiding ability of the SMP device in blood. Surrounding the device with blood increased light leakage, but elimination of the air gap compensated for the extra loss.

Figure 28:
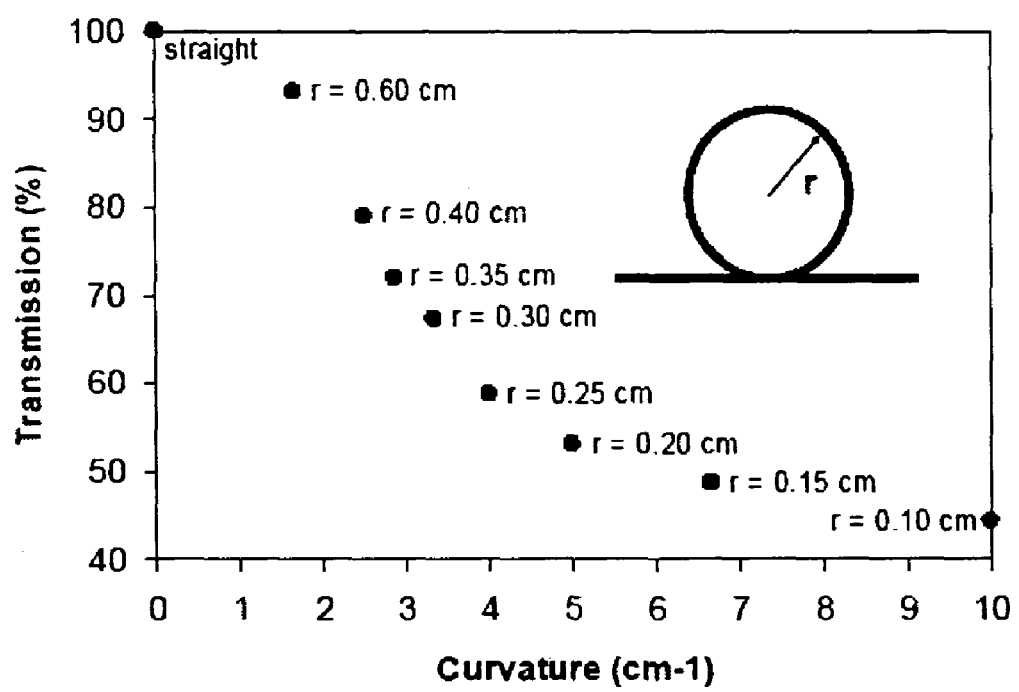
FIG. 28 illustrates light transmission through the optical fiber as a function of fiber curvature.

The transmission of 800 nm laser light through the optical fiber with a single 360° loop versus loop curvature is shown in FIG. 28. Approximately 80% of the light is transmitted for a loop radius of 4 mm, and over 90% of the light is transmitted when the radius is increased to 6 mm.

Referring now to FIG. 28, transmission of 800 nm laser light through the 100 µm core optical fiber with a single 360° loop plotted as a function of loop curvature, 1/r (data points) is illustrated. The transmission exceeds 90% for loop radii above 6 mm. The transmission drops to 80% at a loop radius of 4 mm.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An actuator for acting upon a material in a vessel, comprising:
   a transport vehicle,
   a shape memory polymer basket operatively connected to said transport vehicle, said shape memory polymer basket adapted to move from a first collapsed tubular shape that can be moved through said vessel, to a second open basket shape for acting upon said material,
   wherein said shape memory polymer basket has an attachment portion and an expandable basket portion, wherein said expandable basket portion has a multiplicity of individual and separate leaves, wherein each of said individual and separate leaves has a body with an edge and wherein said body has a slit located entirely within said body extending substantially throughout said body and terminating before reaching said edge, wherein said individual and separate leaves have a width that forms a solid wall when said shape memory polymer basket is in said first collapsed tubular shape, and a heat transfer mechanism operatively connected to said shape memory polymer basket, adapted to transfer heat to said shape memory polymer basket to move said shape memory polymer basket portion from said first collapsed tubular shape to said second open basket shape.

2. The actuator for acting upon a material in a vessel of claim 1 wherein said slits within said bodies of said individual and separate leaves are parallel.

* * * * *